United States Patent
Subramanian et al.

(10) Patent No.: US 11,030,581 B2
(45) Date of Patent: *Jun. 8, 2021

(54) MEDICAL CLAIMS LEAD SUMMARY REPORT GENERATION

(71) Applicant: Palantir Technologies Inc., Palo Alto, CA (US)

(72) Inventors: Gokul Subramanian, McLean, VA (US); Rahul Agarwal, New York City, NY (US); William Seaton, New York City, NY (US); Diane Wu, Palo Alto, CA (US)

(73) Assignee: PALANTIR TECHNOLOGIES INC., Palo Alto, CA (US)

( * ) Notice: Subject to any disclaimer, the term of this patent is extended or adjusted under 35 U.S.C. 154(b) by 39 days.

This patent is subject to a terminal disclaimer.

(21) Appl. No.: 16/457,348

(22) Filed: Jun. 28, 2019

(65) Prior Publication Data

US 2019/0326010 A1 Oct. 24, 2019

Related U.S. Application Data

(63) Continuation of application No. 14/975,697, filed on Dec. 21, 2015, now Pat. No. 10,372,879.

(Continued)

(51) Int. Cl.
*G06Q 10/10* (2012.01)
*G06Q 30/00* (2012.01)
(Continued)

(52) U.S. Cl.
CPC .......... *G06Q 10/10* (2013.01); *G06Q 30/018* (2013.01); *G16H 15/00* (2018.01); *G16H 40/20* (2018.01)

(58) Field of Classification Search
None
See application file for complete search history.

(56) References Cited

U.S. PATENT DOCUMENTS

| 4,899,161 A | 2/1990 | Morin et al. |
| 4,958,305 A | 9/1990 | Piazza |

(Continued)

FOREIGN PATENT DOCUMENTS

| AU | 2012216622 | 5/2015 |
| CN | 101729531 | 6/2010 |

(Continued)

OTHER PUBLICATIONS

U.S. Appl. No. 13/831,791, filed Mar. 15, 2013, Office Action, dated Mar. 4, 2015.

(Continued)

*Primary Examiner* — Christopher Bridges
(74) *Attorney, Agent, or Firm* — Hickman Becker Bingham Ledesma LLP

(57) ABSTRACT

In an embodiment, a computer-implemented method comprises, in response to receiving lead data identifying an entity associated with a health care claim relating to suspected fraud, determining one or more data sources that were used to identify the entity or the suspected fraud; determining a subset of a plurality of data display elements, based on the determined one or more data sources, wherein each of the plurality of data display elements is configured to cause displaying health care claims data associated with the entity in a designated format; automatically obtaining, from a data repository, specific health care claims data associated with the entity for each of the plurality of data display elements in the subset; generating a lead summary report associated with the entity using a report template, the subset, and the obtained specific health care claims data.

20 Claims, 9 Drawing Sheets

Related U.S. Application Data

(60) Provisional application No. 62/099,082, filed on Dec. 31, 2014.

(51) Int. Cl.
  *G16H 15/00* (2018.01)
  *G16H 40/20* (2018.01)

(56) References Cited

U.S. PATENT DOCUMENTS

| | | | |
|---|---|---|---|
| 5,109,399 A | 4/1992 | Thompson | |
| 5,329,108 A | 7/1994 | Lamoure | |
| 5,577,169 A * | 11/1996 | Prezioso | G06Q 10/10 |
| | | | 706/52 |
| 5,632,009 A | 5/1997 | Rao et al. | |
| 5,670,987 A | 9/1997 | Doi et al. | |
| 5,754,182 A | 5/1998 | Kobayashi | |
| 5,781,195 A | 7/1998 | Marvin | |
| 5,781,704 A | 7/1998 | Rossmo | |
| 5,798,769 A | 8/1998 | Chiu et al. | |
| 5,818,737 A | 10/1998 | Orr et al. | |
| 5,845,254 A | 12/1998 | Lockwood et al. | |
| 5,845,300 A | 12/1998 | Comer | |
| 5,893,072 A | 4/1999 | Zizzamia | |
| 6,057,757 A | 5/2000 | Arrowsmith et al. | |
| 6,091,956 A | 7/2000 | Hollenberg | |
| 6,157,747 A | 12/2000 | Szeliski et al. | |
| 6,161,098 A | 12/2000 | Wallman | |
| 6,173,067 B1 | 1/2001 | Payton et al. | |
| 6,178,432 B1 | 1/2001 | Cook et al. | |
| 6,219,053 B1 | 4/2001 | Tachibana et al. | |
| 6,232,971 B1 | 5/2001 | Haynes | |
| 6,247,019 B1 | 6/2001 | Davies | |
| 6,279,018 B1 | 8/2001 | Kudrolli et al. | |
| 6,341,310 B1 | 1/2002 | Leshem et al. | |
| 6,366,933 B1 | 4/2002 | Ball et al. | |
| 6,369,835 B1 | 4/2002 | Lin | |
| 6,389,289 B1 | 5/2002 | Voce et al. | |
| 6,414,683 B1 | 7/2002 | Gueziec | |
| 6,456,997 B1 | 9/2002 | Shukla | |
| 6,483,509 B1 | 11/2002 | Rabenhorst | |
| 6,505,196 B2 | 1/2003 | Drucker et al. | |
| 6,523,019 B1 | 2/2003 | Borthwick | |
| 6,529,900 B1 | 3/2003 | Patterson et al. | |
| 6,549,944 B1 | 4/2003 | Weinberg et al. | |
| 6,560,620 B1 | 5/2003 | Ching | |
| 6,581,068 B1 | 6/2003 | Bensoussan et al. | |
| 6,594,672 B1 | 7/2003 | Lampson et al. | |
| 6,631,496 B1 | 10/2003 | Li et al. | |
| 6,642,945 B1 | 11/2003 | Sharpe | |
| 6,662,103 B1 | 12/2003 | Skolnick et al. | |
| 6,714,936 B1 | 3/2004 | Nevin, III | |
| 6,757,445 B1 | 6/2004 | Knopp | |
| 6,775,675 B1 | 8/2004 | Nwabueze et al. | |
| 6,807,569 B1 | 10/2004 | Bhimani et al. | |
| 6,826,536 B1 * | 11/2004 | Forman | G06Q 40/08 |
| | | | 705/4 |
| 6,828,920 B2 | 12/2004 | Owen et al. | |
| 6,839,745 B1 | 1/2005 | Dingari et al. | |
| 6,877,137 B1 | 4/2005 | Rivette et al. | |
| 6,976,210 B1 | 12/2005 | Silva et al. | |
| 6,980,984 B1 | 12/2005 | Huffman et al. | |
| 6,985,950 B1 | 1/2006 | Hanson et al. | |
| 7,036,085 B2 | 4/2006 | Barros | |
| 7,043,702 B2 | 5/2006 | Chi et al. | |
| 7,055,110 B2 | 5/2006 | Kupka et al. | |
| 7,139,800 B2 | 11/2006 | Bellotti et al. | |
| 7,158,878 B2 | 1/2007 | Rasmussen et al. | |
| 7,162,475 B2 | 1/2007 | Ackerman | |
| 7,168,039 B2 | 1/2007 | Bertram | |
| 7,171,427 B2 | 1/2007 | Witowski et al. | |
| 7,225,468 B2 | 5/2007 | Waisman et al. | |
| 7,269,786 B1 | 9/2007 | Malloy et al. | |
| 7,278,105 B1 | 10/2007 | Kitts | |
| 7,290,698 B2 | 11/2007 | Poslinski et al. | |
| 7,333,998 B2 | 2/2008 | Heckerman et al. | |
| 7,370,047 B2 | 5/2008 | Gorman | |
| 7,375,732 B2 | 5/2008 | Arcas | |
| 7,379,811 B2 | 5/2008 | Rasmussen et al. | |
| 7,379,903 B2 | 5/2008 | Caballero et al. | |
| 7,383,239 B2 | 6/2008 | Bonissone | |
| 7,418,431 B1 * | 8/2008 | Nies | G06F 16/972 |
| | | | 706/21 |
| 7,426,654 B2 | 9/2008 | Adams et al. | |
| 7,454,466 B2 | 11/2008 | Bellotti et al. | |
| 7,457,706 B2 | 11/2008 | Malero et al. | |
| 7,467,375 B2 | 12/2008 | Tondreau et al. | |
| 7,487,139 B2 | 2/2009 | Fraleigh et al. | |
| 7,502,786 B2 | 3/2009 | Liu et al. | |
| 7,519,470 B2 | 4/2009 | Brasche et al. | |
| 7,525,422 B2 | 4/2009 | Bishop et al. | |
| 7,529,195 B2 | 5/2009 | Gorman | |
| 7,529,727 B2 | 5/2009 | Arning et al. | |
| 7,539,666 B2 | 5/2009 | Ashworth et al. | |
| 7,558,677 B2 | 7/2009 | Jones | |
| 7,574,428 B2 | 8/2009 | Leiserowitz et al. | |
| 7,579,965 B2 | 8/2009 | Bucholz | |
| 7,596,285 B2 | 9/2009 | Brown et al. | |
| 7,614,006 B2 | 11/2009 | Molander | |
| 7,617,232 B2 | 11/2009 | Gabbert et al. | |
| 7,620,628 B2 | 11/2009 | Kapur et al. | |
| 7,627,812 B2 | 12/2009 | Chamberlain et al. | |
| 7,634,717 B2 | 12/2009 | Chamberlain et al. | |
| 7,663,621 B1 | 2/2010 | Allen et al. | |
| 7,703,021 B1 | 4/2010 | Flam | |
| 7,712,049 B2 | 5/2010 | Williams et al. | |
| 7,716,077 B1 | 5/2010 | Mikurak | |
| 7,725,530 B2 | 5/2010 | Sah et al. | |
| 7,725,547 B2 | 5/2010 | Albertson et al. | |
| 7,730,082 B2 | 6/2010 | Sah et al. | |
| 7,730,109 B2 | 6/2010 | Rohrs et al. | |
| 7,765,489 B1 | 7/2010 | Shah | |
| 7,770,100 B2 | 8/2010 | Chamberlain et al. | |
| 7,791,616 B2 | 9/2010 | Ioup et al. | |
| 7,802,722 B1 * | 9/2010 | Papierniak | G06Q 10/10 |
| | | | 235/382 |
| 7,805,457 B1 | 9/2010 | Viola et al. | |
| 7,809,703 B2 | 10/2010 | Balabhadrapatruni et al. | |
| 7,813,937 B1 * | 10/2010 | Pathria | G06Q 20/403 |
| | | | 705/2 |
| 7,818,658 B2 | 10/2010 | Chen | |
| 7,827,045 B2 | 11/2010 | Madill et al. | |
| 7,870,493 B2 | 1/2011 | Pall et al. | |
| 7,872,647 B2 | 1/2011 | Mayer et al. | |
| 7,894,984 B2 | 2/2011 | Rasmussen et al. | |
| 7,899,611 B2 | 3/2011 | Downs et al. | |
| 7,917,376 B2 | 3/2011 | Bellin et al. | |
| 7,920,963 B2 | 4/2011 | Jouline et al. | |
| 7,933,862 B2 | 4/2011 | Chamberlain et al. | |
| 7,962,281 B2 | 6/2011 | Rasmussen et al. | |
| 7,962,495 B2 | 6/2011 | Jain et al. | |
| 7,962,848 B2 | 6/2011 | Bertram | |
| 7,966,199 B1 | 6/2011 | Frasher | |
| 7,970,240 B1 | 6/2011 | Chao et al. | |
| 7,971,150 B2 | 6/2011 | Raskutti et al. | |
| 7,984,374 B2 | 7/2011 | Caro et al. | |
| 8,001,465 B2 | 8/2011 | Kudrolli et al. | |
| 8,001,482 B2 | 8/2011 | Bhattiprolu et al. | |
| 8,010,545 B2 | 8/2011 | Stefik et al. | |
| 8,015,487 B2 | 9/2011 | Roy et al. | |
| 8,024,778 B2 | 9/2011 | Cash et al. | |
| 8,036,632 B1 | 10/2011 | Cona et al. | |
| 8,065,080 B2 | 11/2011 | Koch | |
| 8,085,268 B2 | 12/2011 | Carrino et al. | |
| 8,103,543 B1 | 1/2012 | Zwicky | |
| 8,134,457 B2 | 3/2012 | Velipasalar et al. | |
| 8,145,703 B2 | 3/2012 | Frishert et al. | |
| 8,185,819 B2 | 5/2012 | Sah et al. | |
| 8,196,184 B2 | 6/2012 | Amirov et al. | |
| 8,214,232 B2 * | 7/2012 | Tyler | G06Q 10/10 |
| | | | 705/2 |
| 8,214,361 B1 | 7/2012 | Sandler et al. | |
| 8,214,764 B2 | 7/2012 | Gemmell et al. | |
| 8,225,201 B2 | 7/2012 | Michael | |

(56) References Cited

U.S. PATENT DOCUMENTS

| | | |
|---|---|---|
| 8,229,947 B2 | 7/2012 | Fujinaga |
| 8,230,333 B2 | 7/2012 | Decherd et al. |
| 8,239,668 B1 | 8/2012 | Chen et al. |
| 8,271,461 B2 | 9/2012 | Pike et al. |
| 8,280,880 B1 | 10/2012 | Aymeloglu et al. |
| 8,290,942 B2 | 10/2012 | Jones et al. |
| 8,301,464 B1 | 10/2012 | Cave et al. |
| 8,301,904 B1 | 10/2012 | Gryaznov |
| 8,312,367 B2 | 11/2012 | Foster |
| 8,312,546 B2 | 11/2012 | Alme |
| 8,315,890 B2 | 11/2012 | Lynn et al. |
| 8,325,178 B1 | 12/2012 | Doyle, Jr. |
| 8,332,354 B1 | 12/2012 | Chatterjee et al. |
| 8,352,881 B2 | 1/2013 | Champion et al. |
| 8,368,695 B2 | 2/2013 | Howell et al. |
| 8,397,171 B2 | 3/2013 | Klassen et al. |
| 8,400,448 B1 | 3/2013 | Doyle, Jr. |
| 8,407,180 B1 | 3/2013 | Ramesh et al. |
| 8,412,234 B1 | 4/2013 | Gatmir-Motahari et al. |
| 8,412,707 B1 | 4/2013 | Mianji |
| 8,422,825 B1 | 4/2013 | Neophytou et al. |
| 8,447,722 B1 | 5/2013 | Ahuja et al. |
| 8,452,790 B1 | 5/2013 | Mianji |
| 8,463,036 B1 | 6/2013 | Ramesh et al. |
| 8,489,331 B2 | 7/2013 | Kopf et al. |
| 8,489,623 B2 | 7/2013 | Jain et al. |
| 8,489,641 B1 | 7/2013 | Seefeld et al. |
| 8,498,984 B1 | 7/2013 | Hwang et al. |
| 8,508,533 B2 | 8/2013 | Cervelli et al. |
| 8,514,082 B2 | 8/2013 | Cova et al. |
| 8,514,229 B2 | 8/2013 | Cervelli et al. |
| 8,515,207 B2 | 8/2013 | Chau |
| 8,515,912 B2 | 8/2013 | Garrod et al. |
| 8,527,461 B2 | 9/2013 | Ducott, III et al. |
| 8,554,579 B2 | 10/2013 | Tribble et al. |
| 8,554,709 B2 | 10/2013 | Goodson et al. |
| 8,564,596 B2 | 10/2013 | Carrino et al. |
| 8,577,911 B1 | 11/2013 | Stepinski et al. |
| 8,578,500 B2 * | 11/2013 | Long ............... G06Q 10/0635 726/26 |
| 8,589,273 B2 | 11/2013 | Creeden et al. |
| 8,620,641 B2 | 12/2013 | Farnsworth et al. |
| 8,639,522 B2 | 1/2014 | Pathria et al. |
| 8,639,528 B1 | 1/2014 | Cave |
| 8,639,757 B1 | 1/2014 | Zang et al. |
| 8,646,080 B2 | 2/2014 | Williamson et al. |
| 8,655,687 B2 | 2/2014 | Zizzamia |
| 8,660,869 B2 * | 2/2014 | MacIntyre ........... G06Q 10/063 705/7.11 |
| 8,676,857 B1 | 3/2014 | Adams et al. |
| 8,682,696 B1 | 3/2014 | Shanmugam |
| 8,688,607 B2 * | 4/2014 | Pacha ................... G06Q 10/10 706/45 |
| 8,689,108 B1 | 4/2014 | Duffield et al. |
| 8,713,467 B1 | 4/2014 | Goldenberg et al. |
| 8,726,379 B1 | 5/2014 | Stiansen et al. |
| 8,739,278 B2 | 5/2014 | Varghese |
| 8,742,934 B1 | 6/2014 | Sarpy et al. |
| 8,745,516 B2 | 6/2014 | Mason et al. |
| 8,781,169 B2 | 7/2014 | Jackson et al. |
| 8,787,939 B2 | 7/2014 | Papakipos et al. |
| 8,799,313 B2 | 8/2014 | Satlow |
| 8,799,799 B1 | 8/2014 | Cervelli et al. |
| 8,812,960 B1 | 8/2014 | Sun et al. |
| 8,830,322 B2 | 9/2014 | Nerayoff et al. |
| 8,832,594 B1 | 9/2014 | Thompson et al. |
| 8,868,537 B1 | 10/2014 | Colgrove et al. |
| 8,917,274 B2 | 12/2014 | Ma et al. |
| 8,924,872 B1 | 12/2014 | Bogomolov et al. |
| 8,937,619 B2 | 1/2015 | Sharma et al. |
| 8,938,686 B1 | 1/2015 | Erenrich et al. |
| 8,949,164 B1 | 2/2015 | Mohler |
| 9,009,171 B1 | 4/2015 | Grossman et al. |
| 9,009,827 B1 | 4/2015 | Albertson et al. |
| 9,021,260 B1 | 4/2015 | Falk et al. |
| 9,021,384 B1 | 4/2015 | Beard et al. |
| 2002/0003539 A1 | 1/2002 | Abe |
| 2002/0033848 A1 | 3/2002 | Sciammarella et al. |
| 2002/0065708 A1 | 5/2002 | Senay et al. |
| 2002/0091707 A1 | 7/2002 | Keller |
| 2002/0095658 A1 | 7/2002 | Shulman |
| 2002/0116120 A1 | 8/2002 | Ruiz et al. |
| 2002/0130867 A1 | 9/2002 | Yang et al. |
| 2002/0174201 A1 | 11/2002 | Ramer et al. |
| 2002/0194119 A1 | 12/2002 | Wright et al. |
| 2003/0028560 A1 | 2/2003 | Kudrolli et al. |
| 2003/0036927 A1 | 2/2003 | Bowen |
| 2003/0039948 A1 | 2/2003 | Donahue |
| 2003/0052896 A1 | 3/2003 | Higgins et al. |
| 2003/0103049 A1 | 6/2003 | Kindratenko et al. |
| 2003/0139947 A1 | 7/2003 | Alemi et al. |
| 2003/0140106 A1 | 7/2003 | Raguseo |
| 2003/0144868 A1 | 7/2003 | MacIntyre et al. |
| 2003/0154097 A1 | 8/2003 | Hartley et al. |
| 2003/0163352 A1 | 8/2003 | Surpin et al. |
| 2003/0225755 A1 | 12/2003 | Iwayama et al. |
| 2003/0229519 A1 * | 12/2003 | Eidex .................. G16H 50/20 705/2 |
| 2003/0229848 A1 | 12/2003 | Arend et al. |
| 2004/0030492 A1 | 2/2004 | Fox et al. |
| 2004/0032432 A1 | 2/2004 | Baynger |
| 2004/0039498 A1 | 2/2004 | Ollis et al. |
| 2004/0064256 A1 | 4/2004 | Barinek et al. |
| 2004/0078228 A1 | 4/2004 | Fitzgerald et al. |
| 2004/0085318 A1 | 5/2004 | Hassler et al. |
| 2004/0095349 A1 * | 5/2004 | Bito ..................... G06T 11/20 345/440 |
| 2004/0098236 A1 | 5/2004 | Mayer et al. |
| 2004/0111410 A1 | 6/2004 | Burgoon et al. |
| 2004/0126840 A1 | 7/2004 | Cheng et al. |
| 2004/0143602 A1 | 7/2004 | Ruiz et al. |
| 2004/0143796 A1 | 7/2004 | Lerner et al. |
| 2004/0153418 A1 | 8/2004 | Hanweck |
| 2004/0163039 A1 | 8/2004 | Gorman |
| 2004/0193600 A1 | 9/2004 | Kaasten et al. |
| 2004/0221223 A1 | 11/2004 | Yu et al. |
| 2004/0250124 A1 | 12/2004 | Chesla et al. |
| 2004/0260702 A1 | 12/2004 | Cragun et al. |
| 2005/0027705 A1 | 2/2005 | Sadri et al. |
| 2005/0028094 A1 | 2/2005 | Allyn |
| 2005/0031197 A1 | 2/2005 | Knopp |
| 2005/0034062 A1 | 2/2005 | Bufkin et al. |
| 2005/0039119 A1 | 2/2005 | Parks et al. |
| 2005/0080769 A1 | 4/2005 | Gemmell |
| 2005/0086207 A1 | 4/2005 | Heuer et al. |
| 2005/0108063 A1 | 5/2005 | Madill et al. |
| 2005/0125715 A1 | 6/2005 | Di Franco et al. |
| 2005/0149527 A1 | 7/2005 | Berlin |
| 2005/0162523 A1 | 7/2005 | Darrell et al. |
| 2005/0180330 A1 | 8/2005 | Shapiro |
| 2005/0182502 A1 | 8/2005 | Iyengar |
| 2005/0182654 A1 | 8/2005 | Abolfathi et al. |
| 2005/0182793 A1 | 8/2005 | Keenan et al. |
| 2005/0183005 A1 | 8/2005 | Denoue et al. |
| 2005/0229256 A2 | 10/2005 | Banzhof |
| 2005/0246327 A1 | 11/2005 | Yeung et al. |
| 2005/0251786 A1 | 11/2005 | Citron et al. |
| 2005/0267652 A1 | 12/2005 | Allstadt et al. |
| 2006/0026120 A1 | 2/2006 | Carolan et al. |
| 2006/0026170 A1 | 2/2006 | Kreitler et al. |
| 2006/0053096 A1 | 3/2006 | Subramanian et al. |
| 2006/0059139 A1 | 3/2006 | Robinson |
| 2006/0069912 A1 | 3/2006 | Zheng et al. |
| 2006/0074881 A1 | 4/2006 | Vembu et al. |
| 2006/0080139 A1 | 4/2006 | Mainzer |
| 2006/0080619 A1 | 4/2006 | Carlson et al. |
| 2006/0129746 A1 | 6/2006 | Porter |
| 2006/0142949 A1 | 6/2006 | Helt |
| 2006/0146050 A1 | 7/2006 | Yamauchi |
| 2006/0149596 A1 | 7/2006 | Surpin et al. |
| 2006/0178915 A1 | 8/2006 | Chao |
| 2006/0203337 A1 | 9/2006 | White |
| 2006/0218637 A1 | 9/2006 | Thomas et al. |
| 2006/0241974 A1 | 10/2006 | Chao et al. |

(56) References Cited

U.S. PATENT DOCUMENTS

| | | |
|---|---|---|
| 2006/0242040 A1 | 10/2006 | Rader |
| 2006/0242630 A1 | 10/2006 | Koike et al. |
| 2006/0251307 A1 | 11/2006 | Florin et al. |
| 2006/0265747 A1 | 11/2006 | Judge |
| 2006/0271277 A1 | 11/2006 | Hu et al. |
| 2006/0279630 A1 | 12/2006 | Aggarwal et al. |
| 2007/0011150 A1 | 1/2007 | Frank |
| 2007/0016363 A1 | 1/2007 | Huang et al. |
| 2007/0038962 A1 | 2/2007 | Fuchs et al. |
| 2007/0057966 A1 | 3/2007 | Ohno et al. |
| 2007/0078832 A1 | 4/2007 | Ott et al. |
| 2007/0083541 A1 | 4/2007 | Fraleigh et al. |
| 2007/0094389 A1 | 4/2007 | Nussey et al. |
| 2007/0106533 A1 | 5/2007 | Greene |
| 2007/0136095 A1 | 6/2007 | Weinstein |
| 2007/0150369 A1 | 6/2007 | Zivin |
| 2007/0174760 A1 | 7/2007 | Chamberlain et al. |
| 2007/0188516 A1 | 8/2007 | Loup et al. |
| 2007/0192143 A1 | 8/2007 | Krishnan et al. |
| 2007/0192265 A1 | 8/2007 | Chopin et al. |
| 2007/0208497 A1 | 9/2007 | Downs et al. |
| 2007/0208498 A1 | 9/2007 | Barker et al. |
| 2007/0208736 A1 | 9/2007 | Tanigawa et al. |
| 2007/0240062 A1 | 10/2007 | Christena et al. |
| 2007/0258642 A1 | 11/2007 | Thota |
| 2007/0266336 A1 | 11/2007 | Nojima et al. |
| 2007/0294643 A1 | 12/2007 | Kyle |
| 2007/0294766 A1 | 12/2007 | Mir et al. |
| 2007/0299697 A1 | 12/2007 | Friedlander et al. |
| 2008/0010605 A1 | 1/2008 | Frank |
| 2008/0034327 A1 | 2/2008 | Cisler et al. |
| 2008/0040684 A1 | 2/2008 | Crump |
| 2008/0051989 A1 | 2/2008 | Welsh |
| 2008/0077597 A1 | 3/2008 | Butler |
| 2008/0082578 A1 | 4/2008 | Hogue et al. |
| 2008/0098085 A1 | 4/2008 | Krane et al. |
| 2008/0104019 A1 | 5/2008 | Nath |
| 2008/0104101 A1 | 5/2008 | Krishenbaum et al. |
| 2008/0126951 A1 | 5/2008 | Sood et al. |
| 2008/0155440 A1 | 6/2008 | Trevor et al. |
| 2008/0163073 A1 | 7/2008 | Becker et al. |
| 2008/0172257 A1* | 7/2008 | Bisker ............... G06Q 10/10 705/4 |
| 2008/0192053 A1 | 8/2008 | Howell et al. |
| 2008/0195417 A1 | 8/2008 | Surpin et al. |
| 2008/0195421 A1 | 8/2008 | Ludwig et al. |
| 2008/0195608 A1 | 8/2008 | Clover |
| 2008/0222295 A1 | 9/2008 | Robinson et al. |
| 2008/0223834 A1 | 9/2008 | Griffiths et al. |
| 2008/0229056 A1 | 9/2008 | Agarwal et al. |
| 2008/0229422 A1 | 9/2008 | Hudis et al. |
| 2008/0235199 A1 | 9/2008 | Li et al. |
| 2008/0249820 A1 | 10/2008 | Pathria et al. |
| 2008/0255973 A1 | 10/2008 | El Wade et al. |
| 2008/0263468 A1 | 10/2008 | Cappione et al. |
| 2008/0267107 A1 | 10/2008 | Rosenberg |
| 2008/0270468 A1 | 10/2008 | Mao |
| 2008/0276167 A1 | 11/2008 | Michael |
| 2008/0278311 A1 | 11/2008 | Grange et al. |
| 2008/0281819 A1 | 11/2008 | Tenenbaum et al. |
| 2008/0288306 A1 | 11/2008 | MacIntyre et al. |
| 2008/0294678 A1 | 11/2008 | Gorman et al. |
| 2008/0301643 A1 | 12/2008 | Appleton et al. |
| 2009/0002492 A1 | 1/2009 | Velipasalar et al. |
| 2009/0027418 A1 | 1/2009 | Maru et al. |
| 2009/0030915 A1 | 1/2009 | Winter et al. |
| 2009/0043801 A1 | 2/2009 | LeClair |
| 2009/0055251 A1 | 2/2009 | Shah et al. |
| 2009/0070162 A1 | 3/2009 | Leonelli et al. |
| 2009/0088964 A1 | 4/2009 | Schaaf et al. |
| 2009/0100018 A1 | 4/2009 | Roberts |
| 2009/0103442 A1 | 4/2009 | Douville |
| 2009/0115786 A1 | 5/2009 | Shmiasaki et al. |
| 2009/0125348 A1 | 5/2009 | Rastogi |
| 2009/0125369 A1 | 5/2009 | Kloosstra et al. |
| 2009/0125459 A1 | 5/2009 | Norton et al. |
| 2009/0132921 A1 | 5/2009 | Hwangbo et al. |
| 2009/0132953 A1 | 5/2009 | Reed et al. |
| 2009/0144262 A1 | 6/2009 | White et al. |
| 2009/0144274 A1 | 6/2009 | Fraleigh et al. |
| 2009/0158185 A1 | 6/2009 | Lacevic et al. |
| 2009/0164934 A1 | 6/2009 | Bhattiprolu et al. |
| 2009/0171939 A1 | 7/2009 | Athsani et al. |
| 2009/0172511 A1 | 7/2009 | Decherd et al. |
| 2009/0177962 A1 | 7/2009 | Gusmorino et al. |
| 2009/0179892 A1 | 7/2009 | Tsuda et al. |
| 2009/0198641 A1 | 8/2009 | Tortoriello |
| 2009/0216562 A1 | 8/2009 | Faulkner et al. |
| 2009/0222400 A1 | 9/2009 | Kupershmidt et al. |
| 2009/0222760 A1 | 9/2009 | Halverson et al. |
| 2009/0234720 A1 | 9/2009 | George et al. |
| 2009/0235084 A1* | 9/2009 | Ferraro ............... G06Q 10/10 713/182 |
| 2009/0240529 A1 | 9/2009 | Chess et al. |
| 2009/0249244 A1 | 10/2009 | Robinson et al. |
| 2009/0281839 A1 | 11/2009 | Lynn et al. |
| 2009/0287470 A1 | 11/2009 | Farnsworth et al. |
| 2009/0292626 A1 | 11/2009 | Oxford |
| 2009/0319295 A1 | 12/2009 | Kass-Hout et al. |
| 2009/0328222 A1 | 12/2009 | Helman et al. |
| 2010/0011282 A1 | 1/2010 | Dollard et al. |
| 2010/0042922 A1 | 2/2010 | Bradateanu et al. |
| 2010/0306713 A1 | 2/2010 | Geisner et al. |
| 2010/0057716 A1 | 3/2010 | Stefik et al. |
| 2010/0063961 A1 | 3/2010 | Guiheneuf et al. |
| 2010/0070523 A1 | 3/2010 | Delgo et al. |
| 2010/0070842 A1 | 3/2010 | Aymeloglu et al. |
| 2010/0070845 A1 | 3/2010 | Facemire et al. |
| 2010/0070897 A1 | 3/2010 | Aymeloglu et al. |
| 2010/0076968 A1 | 3/2010 | Boyns et al. |
| 2010/0077481 A1 | 3/2010 | Polyakov et al. |
| 2010/0100963 A1 | 4/2010 | Mahaffey |
| 2010/0103124 A1 | 4/2010 | Kruzeniski et al. |
| 2010/0106420 A1 | 4/2010 | Mattikalli et al. |
| 2010/0114887 A1 | 5/2010 | Conway et al. |
| 2010/0122152 A1 | 5/2010 | Chamberlain et al. |
| 2010/0131457 A1 | 5/2010 | Heimendinger |
| 2010/0162176 A1 | 6/2010 | Dunton |
| 2010/0191563 A1 | 7/2010 | Schlaifer et al. |
| 2010/0198684 A1 | 8/2010 | Eraker et al. |
| 2010/0199225 A1 | 8/2010 | Coleman et al. |
| 2010/0228812 A1 | 9/2010 | Uomini |
| 2010/0235197 A1 | 9/2010 | Dang |
| 2010/0235915 A1 | 9/2010 | Memon et al. |
| 2010/0250412 A1 | 9/2010 | Wagner |
| 2010/0257515 A1 | 10/2010 | Bates et al. |
| 2010/0262688 A1 | 10/2010 | Hussain et al. |
| 2010/0274580 A1 | 10/2010 | Crownover et al. |
| 2010/0280851 A1 | 11/2010 | Merkin |
| 2010/0280857 A1 | 11/2010 | Liu et al. |
| 2010/0293174 A1 | 11/2010 | Bennett et al. |
| 2010/0313119 A1 | 12/2010 | Baldwin et al. |
| 2010/0318924 A1 | 12/2010 | Frankel et al. |
| 2010/0321399 A1 | 12/2010 | Ellren et al. |
| 2010/0324929 A1 | 12/2010 | Petrasich et al. |
| 2010/0325526 A1 | 12/2010 | Ellis et al. |
| 2010/0325581 A1 | 12/2010 | Finkelstein et al. |
| 2010/0330801 A1 | 12/2010 | Rouh |
| 2011/0022312 A1 | 1/2011 | McDonough et al. |
| 2011/0029526 A1 | 2/2011 | Knight et al. |
| 2011/0047159 A1 | 2/2011 | Baid et al. |
| 2011/0060753 A1 | 3/2011 | Shaked et al. |
| 2011/0061013 A1 | 3/2011 | Bilicki et al. |
| 2011/0069145 A1 | 3/2011 | Weber et al. |
| 2011/0074811 A1 | 3/2011 | Hanson et al. |
| 2011/0078055 A1 | 3/2011 | Faribault et al. |
| 2011/0078173 A1 | 3/2011 | Seligmann et al. |
| 2011/0117878 A1 | 5/2011 | Barash et al. |
| 2011/0119100 A1 | 5/2011 | Ruhl et al. |
| 2011/0137766 A1 | 6/2011 | Rasmussen et al. |
| 2011/0153384 A1 | 6/2011 | Horne et al. |
| 2011/0161096 A1 | 6/2011 | Buehler et al. |
| 2011/0161409 A1 | 6/2011 | Nair |
| 2011/0167105 A1 | 7/2011 | Ramakrishnan et al. |

(56) References Cited

U.S. PATENT DOCUMENTS

| | | |
|---|---|---|
| 2011/0170799 A1 | 7/2011 | Carrino et al. |
| 2011/0173032 A1 | 7/2011 | Payne et al. |
| 2011/0179048 A1 | 7/2011 | Satlow |
| 2011/0185316 A1 | 7/2011 | Reid et al. |
| 2011/0191284 A1 | 8/2011 | Dalton |
| 2011/0208724 A1 | 8/2011 | Jones et al. |
| 2011/0218934 A1 | 9/2011 | Elser |
| 2011/0219450 A1 | 9/2011 | McDougal et al. |
| 2011/0225198 A1 | 9/2011 | Edwards et al. |
| 2011/0238553 A1 | 9/2011 | Raj et al. |
| 2011/0246229 A1 | 10/2011 | Pacha |
| 2011/0258158 A1 | 10/2011 | Resende et al. |
| 2011/0270705 A1 | 11/2011 | Parker |
| 2011/0289397 A1 | 11/2011 | Eastmond et al. |
| 2011/0289407 A1 | 11/2011 | Naik et al. |
| 2011/0291851 A1 | 12/2011 | Whisenant |
| 2011/0310005 A1 | 12/2011 | Chen et al. |
| 2011/0314007 A1 | 12/2011 | Dassa et al. |
| 2012/0004894 A1 | 1/2012 | Butler |
| 2012/0016688 A1 | 1/2012 | Perrin et al. |
| 2012/0019559 A1 | 1/2012 | Siler et al. |
| 2012/0036013 A1 | 2/2012 | Neuhaus et al. |
| 2012/0036434 A1 | 2/2012 | Oberstein |
| 2012/0050293 A1 | 3/2012 | Carlhian et al. |
| 2012/0065987 A1 | 3/2012 | Farooq et al. |
| 2012/0066296 A1 | 3/2012 | Appleton et al. |
| 2012/0072825 A1 | 3/2012 | Sherkin et al. |
| 2012/0079363 A1 | 3/2012 | Folting et al. |
| 2012/0084184 A1 | 4/2012 | Raleigh |
| 2012/0106801 A1 | 5/2012 | Jackson |
| 2012/0110633 A1 | 5/2012 | An et al. |
| 2012/0110674 A1 | 5/2012 | Belani et al. |
| 2012/0117082 A1 | 5/2012 | Koperda et al. |
| 2012/0130937 A1 | 5/2012 | Leon et al. |
| 2012/0131507 A1 | 5/2012 | Sparandara et al. |
| 2012/0131512 A1 | 5/2012 | Takeuchi et al. |
| 2012/0144335 A1 | 6/2012 | Abeln et al. |
| 2012/0158572 A1 | 6/2012 | Dorai et al. |
| 2012/0159307 A1 | 6/2012 | Chung et al. |
| 2012/0159362 A1 | 6/2012 | Brown et al. |
| 2012/0159363 A1 | 6/2012 | DeBacker et al. |
| 2012/0159399 A1 | 6/2012 | Bastide et al. |
| 2012/0173280 A1 | 7/2012 | Gustafson et al. |
| 2012/0173289 A1* | 7/2012 | Pollard .................. G06Q 40/08 705/4 |
| 2012/0173985 A1 | 7/2012 | Peppel |
| 2012/0196557 A1 | 8/2012 | Reich et al. |
| 2012/0196558 A1 | 8/2012 | Reich et al. |
| 2012/0197657 A1 | 8/2012 | Prodanovic |
| 2012/0197660 A1 | 8/2012 | Prodanovic |
| 2012/0206469 A1 | 8/2012 | Hulubei et al. |
| 2012/0208636 A1 | 8/2012 | Feige |
| 2012/0221511 A1 | 8/2012 | Gibson et al. |
| 2012/0221553 A1 | 8/2012 | Wittmer et al. |
| 2012/0221580 A1 | 8/2012 | Barney |
| 2012/0245976 A1 | 9/2012 | Kumar et al. |
| 2012/0246148 A1 | 9/2012 | Dror |
| 2012/0254129 A1 | 10/2012 | Wheeler et al. |
| 2012/0284345 A1 | 11/2012 | Costenaro et al. |
| 2012/0290879 A1 | 11/2012 | Shibuya et al. |
| 2012/0296907 A1 | 11/2012 | Long et al. |
| 2012/0310661 A1 | 12/2012 | Greene |
| 2012/0311684 A1 | 12/2012 | Paulsen et al. |
| 2012/0323888 A1 | 12/2012 | Osann, Jr. |
| 2012/0330973 A1 | 12/2012 | Ghuneim et al. |
| 2013/0006655 A1 | 1/2013 | Van Arkel et al. |
| 2013/0006668 A1* | 1/2013 | Van Arkel .............. G06Q 10/10 705/3 |
| 2013/0006725 A1 | 1/2013 | Simanek et al. |
| 2013/0018796 A1 | 1/2013 | Kolhatkar et al. |
| 2013/0019306 A1 | 1/2013 | Lagar-Cavilla et al. |
| 2013/0046842 A1 | 2/2013 | Muntz et al. |
| 2013/0057551 A1 | 3/2013 | Ebert et al. |
| 2013/0060786 A1 | 3/2013 | Serrano et al. |
| 2013/0061169 A1 | 3/2013 | Pearcy et al. |
| 2013/0073377 A1 | 3/2013 | Heath |
| 2013/0073454 A1 | 3/2013 | Busch |
| 2013/0078943 A1 | 3/2013 | Biage et al. |
| 2013/0097482 A1 | 4/2013 | Marantz et al. |
| 2013/0101159 A1 | 4/2013 | Chao et al. |
| 2013/0110822 A1 | 5/2013 | Ikeda et al. |
| 2013/0110877 A1 | 5/2013 | Bonham et al. |
| 2013/0111320 A1 | 5/2013 | Campbell et al. |
| 2013/0117651 A1 | 5/2013 | Waldman et al. |
| 2013/0139268 A1 | 5/2013 | An et al. |
| 2013/0150004 A1 | 6/2013 | Rosen |
| 2013/0151148 A1 | 6/2013 | Parundekar et al. |
| 2013/0157234 A1 | 6/2013 | Gulli et al. |
| 2013/0166550 A1 | 6/2013 | Buchmann et al. |
| 2013/0176321 A1 | 7/2013 | Mitchell et al. |
| 2013/0179420 A1 | 7/2013 | Park et al. |
| 2013/0224696 A1 | 8/2013 | Wolfe et al. |
| 2013/0226953 A1 | 8/2013 | Markovich et al. |
| 2013/0238616 A1 | 9/2013 | Rose et al. |
| 2013/0246170 A1 | 9/2013 | Gross et al. |
| 2013/0251233 A1 | 9/2013 | Yang et al. |
| 2013/0262527 A1 | 10/2013 | Hunter et al. |
| 2013/0263019 A1 | 10/2013 | Castellanos et al. |
| 2013/0267207 A1 | 10/2013 | Hao et al. |
| 2013/0268520 A1 | 10/2013 | Fisher et al. |
| 2013/0276799 A1 | 10/2013 | Davison |
| 2013/0279757 A1 | 10/2013 | Kephart |
| 2013/0282696 A1 | 10/2013 | John et al. |
| 2013/0282723 A1 | 10/2013 | Petersen et al. |
| 2013/0290011 A1 | 10/2013 | Lynn et al. |
| 2013/0290825 A1 | 10/2013 | Arndt et al. |
| 2013/0297619 A1 | 11/2013 | Chandarsekaran et al. |
| 2013/0311375 A1 | 11/2013 | Priebatsch |
| 2014/0019936 A1 | 1/2014 | Cohanoff |
| 2014/0032506 A1 | 1/2014 | Hoey et al. |
| 2014/0033010 A1 | 1/2014 | Richardt et al. |
| 2014/0040371 A1 | 2/2014 | Gurevich et al. |
| 2014/0047357 A1 | 2/2014 | Alfaro et al. |
| 2014/0052466 A1 | 2/2014 | DeVille et al. |
| 2014/0058754 A1 | 2/2014 | Wild |
| 2014/0058763 A1* | 2/2014 | Zizzamia ............... G06Q 40/08 705/4 |
| 2014/0059038 A1 | 2/2014 | McPherson et al. |
| 2014/0059683 A1 | 2/2014 | Ashley |
| 2014/0068487 A1 | 3/2014 | Steiger et al. |
| 2014/0081652 A1* | 3/2014 | Klindworth ........ G06Q 20/4016 705/2 |
| 2014/0095273 A1 | 4/2014 | Tang et al. |
| 2014/0095509 A1 | 4/2014 | Patton |
| 2014/0108068 A1 | 4/2014 | Williams |
| 2014/0108380 A1 | 4/2014 | Gotz et al. |
| 2014/0108985 A1 | 4/2014 | Scott et al. |
| 2014/0123279 A1 | 5/2014 | Bishop et al. |
| 2014/0129256 A1* | 5/2014 | Veren .................... G06Q 40/08 705/3 |
| 2014/0129261 A1 | 5/2014 | Bothwell et al. |
| 2014/0136237 A1 | 5/2014 | Anderson et al. |
| 2014/0149130 A1 | 5/2014 | Getchius |
| 2014/0149142 A1* | 5/2014 | P .......................... G06Q 10/10 705/3 |
| 2014/0149436 A1 | 5/2014 | Bahrami et al. |
| 2014/0156527 A1 | 6/2014 | Grigg et al. |
| 2014/0157172 A1 | 6/2014 | Peery et al. |
| 2014/0164502 A1 | 6/2014 | Khodorenko et al. |
| 2014/0172439 A1* | 6/2014 | Conway ................ G06Q 10/10 705/2 |
| 2014/0189536 A1 | 7/2014 | Lange et al. |
| 2014/0195515 A1 | 7/2014 | Baker et al. |
| 2014/0195887 A1 | 7/2014 | Ellis et al. |
| 2014/0214579 A1 | 7/2014 | Shen et al. |
| 2014/0244284 A1 | 8/2014 | Smith |
| 2014/0257846 A1* | 9/2014 | Hermiz ................. G06Q 40/08 705/3 |
| 2014/0267294 A1 | 9/2014 | Ma |
| 2014/0267295 A1 | 9/2014 | Sharma |
| 2014/0278479 A1 | 9/2014 | Wang et al. |
| 2014/0279824 A1 | 9/2014 | Tamayo |
| 2014/0316911 A1 | 10/2014 | Gross |
| 2014/0333651 A1 | 11/2014 | Cervelli et al. |

(56) References Cited

U.S. PATENT DOCUMENTS

| | | |
|---|---|---|
| 2014/0337772 A1 | 11/2014 | Cervelli et al. |
| 2014/0357961 A1 | 12/2014 | Meltzer et al. |
| 2014/0358579 A1 | 12/2014 | Nikolova-Simons et al. |
| 2014/0361899 A1 | 12/2014 | Layson |
| 2014/0366132 A1 | 12/2014 | Stiansen et al. |
| 2015/0019394 A1 | 1/2015 | Unser et al. |
| 2015/0029176 A1 | 1/2015 | Baxter et al. |
| 2015/0046181 A1* | 2/2015 | Adjaoute ............ G06N 5/04 705/2 |
| 2015/0046870 A1 | 2/2015 | Goldenberg et al. |
| 2015/0089424 A1 | 3/2015 | Duffield et al. |
| 2015/0100897 A1 | 4/2015 | Sun et al. |
| 2015/0100907 A1 | 4/2015 | Erenrich et al. |
| 2015/0134666 A1 | 5/2015 | Gattiker et al. |
| 2015/0169709 A1 | 6/2015 | Kara et al. |
| 2015/0169726 A1 | 6/2015 | Kara et al. |
| 2015/0170077 A1 | 6/2015 | Kara et al. |
| 2015/0178877 A1 | 6/2015 | Bogomolov et al. |
| 2015/0186821 A1 | 7/2015 | Wang et al. |
| 2015/0187036 A1 | 7/2015 | Wang et al. |
| 2015/0235334 A1 | 8/2015 | Wang et al. |
| 2015/0310180 A1 | 10/2015 | Pattekar et al. |
| 2016/0034578 A1 | 2/2016 | Wang et al. |
| 2016/0063193 A1 | 3/2016 | Freese et al. |
| 2016/0188819 A1 | 6/2016 | Subramanian et al. |
| 2016/0267484 A1* | 9/2016 | Smoley ............... G06Q 40/08 |

FOREIGN PATENT DOCUMENTS

| | | |
|---|---|---|
| CN | 103281301 | 9/2013 |
| DE | 10201403476 | 9/2014 |
| DE | 102014103482 | 9/2014 |
| DE | 102013222023 | 1/2015 |
| DE | 102014215621 | 2/2015 |
| EP | 0 763 201 | 3/1997 |
| EP | 1672527 | 6/2006 |
| EP | 2551799 | 1/2013 |
| EP | 2560134 | 2/2013 |
| EP | 2 575 107 | 4/2013 |
| EP | 2778977 | 9/2014 |
| EP | 2835745 | 2/2015 |
| EP | 2835770 | 2/2015 |
| EP | 2838039 | 2/2015 |
| EP | 2846241 | 3/2015 |
| EP | 2851852 | 3/2015 |
| EP | 2858014 | 4/2015 |
| EP | 2858018 | 4/2015 |
| EP | 2863326 | 4/2015 |
| EP | 2863346 | 4/2015 |
| EP | 2869211 | 5/2015 |
| EP | 2881868 | 6/2015 |
| EP | 2884439 | 6/2015 |
| EP | 2884440 | 6/2015 |
| EP | 2891992 | 7/2015 |
| EP | 2980748 | 2/2016 |
| GB | 2514239 | 11/2014 |
| GB | 2516155 | 1/2015 |
| GB | 2518745 | 4/2015 |
| NL | 2012778 | 11/2014 |
| NL | 2013306 | 2/2015 |
| NZ | 624557 | 12/2014 |
| WO | WO 95/032424 | 11/1995 |
| WO | WO 2000/009529 | 2/2000 |
| WO | WO 2004/057268 | 7/2004 |
| WO | WO 2005/013200 | 2/2005 |
| WO | WO 2005/104736 | 11/2005 |
| WO | WO2008/113059 | 9/2008 |
| WO | WO 2009/061501 | 5/2009 |
| WO | WO 2009/123975 | 10/2009 |
| WO | WO 2010/000014 | 1/2010 |
| WO | WO2010/030913 | 3/2010 |
| WO | WO 2011/058507 | 5/2011 |
| WO | WO 2013/010157 | 1/2013 |
| WO | WO 2013/102892 | 7/2013 |

OTHER PUBLICATIONS

U.S. Appl. No. 14/473,552, filed Aug. 29, 2014, Interview Summary, dated Feb. 24, 2015.

U.S. Appl. No. 14/170,562, filed Jan. 31, 2014, 1st Action Interview Office Action, dated Jul. 7, 2014.

U.S. Appl. No. 14/135,289, filed Dec. 19, 2013, Notice of Allowance, dated Oct. 14, 2014.

U.S. Appl. No. 13/839,026, filed Mar. 15, 2013, Restriction Requirement, dated Apr. 2, 2015.

U.S. Appl. No. 14/289,596, filed May 28, 2014, Office Action, dated May 9, 2016.

U.S. Appl. No. 14/319,765, filed Jun. 30, 2014, Final Office Action, dated Jun. 16, 2015.

U.S. Appl. No. 14/306,147, filed Jun. 16, 2014, Final Office Action, dated Feb. 19, 2015.

U.S. Appl. No. 14/225,006, filed Mar. 25, 2014, First Action Interview, dated Feb. 27, 2015.

U.S. Appl. No. 14/306,154, filed Jun. 16, 2014, Advisory Action, dated May 15, 2015.

U.S. Appl. No. 14/225,160, filed Mar. 25, 2014, Final Office Action, dated Feb. 11, 2015.

U.S. Appl. No. 14/306,138, filed Jun. 16, 2014, Office Action, dated May 26, 2015.

U.S. Appl. No. 14/306,147, filed Jun. 16, 2014, First Office Action Interview, dated Sep. 9, 2014.

U.S. Appl. No. 14/504,103, filed Oct. 1, 2014, First Action Interview, dated Feb. 5, 2015.

U.S. Appl. No. 14/225,160, filed Mar. 25, 2014, First Action Interview, dated Jul. 29, 2014.

U.S. Appl. No. 14/148,568, filed Jan. 6, 2014, Office Action, dated Mar. 26, 2015.

U.S. Appl. No. 14/319,765, filed Jun. 30, 2014, First Office Action Interview, dated Nov. 25, 2014.

U.S. Appl. No. 14/323,935, filed Jul. 3, 2014, Office Action, dated Jun. 22, 2015.

U.S. Appl. No. 14/449,083, filed Jul. 31, 2014, Office Action, dated Apr. 8, 2016.

U.S. Appl. No. 14/225,006, dated Mar. 25, 2014, First Office Action Interview, dated Sep. 10, 2014.

U.S. Appl. No. 14/616,080, filed Feb. 6, 2015, Notice of Allowance, dated Apr. 2, 2015.

U.S. Appl. No. 14/486,991, filed Sep. 15, 2014, Notice of Allowance, dated May 1, 2015.

U.S. Appl. No. 14/225,084, filed Mar. 25, 2014, First Office Action Interview, dated Sep. 2, 2014.

U.S. Appl. No. 14/196,814, filed Mar. 4, 2014, Office Action, dated May 5, 2015.

U.S. Appl. No. 14/323,935, filed Jul. 30, 2014, First Action Interview, dated Nov. 28, 2014.

U.S. Appl. No. 14/449,083, filed Jul. 31, 2014, Office Action, dated Nov. 3, 2016.

U.S. Appl. No. 14/323,935, filed Jul. 30, 2014, Office Action, dated Jun. 22, 2015.

U.S. Appl. No. 14/306,154, filed Jun. 16, 2014, Final Office Action, dated Mar. 11, 2015.

U.S. Appl. No. 14/269,964, filed May 2, 2014, First Action Interview, dated Sep. 3, 2014.

U.S. Appl. No. 13/835,688, filed Mar. 15, 2013, First Action Interview, dated Jun. 17, 2015.

U.S. Appl. No. 14/975,215, filed Dec. 18, 2015, First Office Action Interview, dated May 19, 2016.

U.S. Appl. No. 14/319,765, filed Jun. 30, 2014, First Office Action Interview, dated Feb. 4, 2015.

U.S. Appl. No. 14/326,738, filed Jul. 9, 2014, First Office Action Interview, dated Mar. 31, 2015.

U.S. Appl. No. 14/294,098, filed Jun. 2, 2014, Final Office Action, dated Nov. 6, 2014.

U.S. Appl. No. 14/225,084, filed Mar. 25, 2014, Notice of Allowance, dated May 4, 2015.

U.S. Appl. No. 14/579,752, filed Dec. 22, 2014, First Office Action Interview, dated May 26, 2015.

(56) References Cited

OTHER PUBLICATIONS

U.S. Appl. No. 14/319,765, filed Jun. 30, 2014, Notice of Allowance, dated Nov. 25, 2014.
U.S. Appl. No. 14/294,098, filed Jun. 2, 2014, First Office Action Interview, dated Aug. 15, 2014.
U.S. Appl. No. 14/225,084, filed Mar. 25, 2014, First Office Action Interview, dated Feb. 20, 2015.
U.S. Appl. No. 14/326,738, filed Jul. 9, 2014, First Office Action Interview, dated Dec. 2, 2014.
U.S. Appl. No. 14/473,860, filed Aug. 29, 2014, Notice of Allowance, dated Jan. 5, 2015.
U.S. Appl. No. 14/490,612, filed Sep. 18, 2014, First Office Action Interview, dated Mar. 31, 2015.
U.S. Appl. No. 13/831,791, filed Mar. 15, 2013, Office Action, dated Feb. 11, 2016.
U.S. Appl. No. 12/840,673, filed Jul. 21, 2010, Final Office Action, dated Jan. 2, 2015.
U.S. Appl. No. 13/728,879, filed Dec. 27, 2012, Interview Summary, dated Mar. 17, 2015.
U.S. Appl. No. 14/473,552, fied Aug. 29, 2014, Interview Summary, dated Feb. 24, 2015.
U.S. Appl. No. 14/225,006, filed Mar. 25, 2014, First Office Action Interview, dated Feb. 27, 2015.
U.S. Appl. No. 14/504,103, filed Oct. 1, 2014, Notice of Allowance, dated May 18, 2015.
U.S. Appl. No. 14/490,612, filed Sep. 18, 2014, First Office Action Interview, dated Jan. 27, 2015.
U.S. Appl. No. 13/247,987, filed Sep. 28, 2011, Office Action, dated Apr. 2, 2015.
U.S. Appl. No. 14/306,154, filed Jun. 16, 2014, First Office Action Interview, dated Sep. 9, 2014.
U.S. Appl. No. 14/170,564, filed Jan. 31, 2014, Interview Summary, dated Sep. 30, 2016.
U.S. Appl. No. 12/840,673, filed Jul. 21, 2010, Office Action, dated Sep. 17, 2014.
U.S. Appl. No. 14/306,138, filed Jun. 16, 2014, First Office Action Interview, dated Sep. 23, 2014.
U.S. Appl. No. 14/805,313, filed Jul. 21, 2015, Notice of Allowance, dated Jun. 15, 2016.
U.S. Appl. No. 14/639,606, filed Mar. 5, 2015, First Office Action Interview, dated May 18, 2015.
U.S. Appl. No. 14/225,160, filed Mar. 25, 2014, First Office Action Interview, dated Oct. 22, 2014.
U.S. Appl. No. 14/225,160, filed Mar. 25, 2014, Advisory Action, dated May 20, 2015.
U.S. Appl. No. 14/306,138, filed Jun. 16, 2014, First Office Action Interview, dated Sep. 23, 2015.
U.S. Appl. No. 13/948,859, filed Jul. 23, 2013, Notice of Allowance, dated Dec. 10, 2014.
U.S. Appl. No. 14/486,991, filed Sep. 15, 2014, Office Action, dated Mar. 10, 2015.
U.S. Appl. No. 14/504,103, filed Oct. 1, 2014, First Office Action Interview, dated Mar. 31, 2015.
U.S. Appl. No. 14/170,562, filed Jan. 31, 2014, Final Office Action, dated Mar. 3, 2016.
U.S. Appl. No. 14/323,935, filed Jul. 3, 2014, First Office Action Interview, dated Mar. 31, 2015.
U.S. Appl. No. 14/805,313, filed Jul. 21, 2015, Office Action, dated Dec. 30, 2015.
U.S. Appl. No. 13/839,026, filed Mar. 15, 2013, Restriction Requirement, dated Aug. 4, 2015.
U.S. Appl. No. 14/958,855, filed Dec. 3, 2015, First Office Action Interview, dated May 4, 2016.
U.S. Appl. No. 14/289,596, filed May 28, 2014, Advisory Action, dated Apr. 30, 2015.
U.S. Appl. No. 13/728,879, filed Dec. 27, 2012, First Office Action Interview, dated Jan. 27, 2015.
U.S. Appl. No. 12/840,673, filed Jul. 21, 2010, Notice of Allowance, dated Apr. 6, 2015.
U.S. Appl. No. 14/294,098, filed Jun. 2, 2014, Notice of Allowance, dated Dec. 29, 2014.
U.S. Appl. No. 14/102,394, filed Dec. 10, 2013, Notice of Allowance, dated Aug. 25, 2014.
U.S. Appl. No. 14/479,863, filed Sep. 8, 2014, First Office Action Interview, dated Dec. 26, 2014.
U.S. Appl. No. 14/148,568, filed Jan. 6, 2014, Office Action, dated Oct. 22, 2014.
U.S. Appl. No. 14/291,098, filed Jun. 2, 2014, Final Office Action, dated Nov. 6, 2014.
U.S. Appl. No. 14/192,767, filed Feb. 27, 2014, Notice of Allowance, dated Dec. 16, 2014.
U.S. Appl. No. 14/170,562, filed Jan. 31, 2014, Interview Summary, dated Apr. 29, 2016.
U.S. Appl. No. 14/319,161, filed Jun. 30, 2014, Notice of Allowance, dated May 4, 2015.
U.S. Appl. No. 14/108,187, filed Dec. 16, 2013, Notice of Allowance, dated Aug. 29, 2014.
U.S. Appl. No. 14/306,138, filed Jun. 16, 2014, Final Office Action, dated Feb. 18, 2015.
U.S. Appl. No. 13/835,688, filed Mar. 15, 2013, Office Action, dated Jun. 7, 2016.
U.S. Appl. No. 14/280,490, filed May 16, 2014, First Office Action Interview, dated Jul. 24, 2014.
U.S. Appl. No. 15/085,557, filed Mar. 30, 2016, First Office Action Interview, dated Sep. 14, 2016.
U.S. Appl. No. 14/268,964, filed May 2, 2014, Notice of Allowance, dated Dec. 3, 2014.
U.S. Appl. No. 14/319,161, filed Jun. 30, 2014, Final Office Action, dated Jan. 23, 2015.
U.S. Appl. No. 14/553,433, filed Nov. 5, 2014, Office Action, dated Feb. 26, 2015.
U.S. Appl. No. 14/170,564, filed Jan. 31, 2014, Final Office Action, dated Jan. 12, 2017.
U.S. Appl. No. 14/170,564, filed Jan. 31, 2014, Office Action, dated Mar. 9, 2017.
U.S. Appl. No. 14/170,564, filed Jan. 31, 2014, Office Action, dated Dec. 20, 2016.
U.S. Appl. No. 14/170,566, filed Jan. 31, 2014, Office Action, dated Jan. 11, 2017.
U.S. Appl. No. 13/831,791, filed Mar. 15, 2013, Office Action, dated Aug. 6, 2015.
U.S. Appl. No. 14/170,562, filed Jan. 31, 2014, Interview Summary, dated Oct. 2, 2015.
U.S. Appl. No. 14/289,599, filed May 28, 2014, Final Office Action, dated May 29, 2015.
U.S. Appl. No. 14/289,599, filed May 28, 2014, Advisory Action, dated Sep. 4, 2015.
U.S. Appl. No. 13/949,043, filed Jul. 23, 2013, Office Action, dated Jan. 15, 2016.
U.S. Appl. No. 14/518,757, filed Oct. 20, 2014, First Office Action Interview, dated Apr. 2, 2015.
U.S. Appl. No. 14/449,083, filed Jul. 31, 2014, Office Action, dated Mar. 12, 2015.
U.S. Appl. No. 14/449,083, filed Jul. 31, 2014, First Office Action Interview, dated Oct. 2, 2014.
U.S. Appl. No. 14/289,596, filed May 28, 2014, Final Office Action, dated Jan. 26, 2015.
U.S. Appl. No. 14/289,596, filed May 28, 2014, Office Action, dated Jul. 18, 2014.
U.S. Appl. No. 14/289,599, filed May 28, 2014, Office Action, dated Jul. 22, 2014.
U.S. Appl. No. 14/170,562, filed Jan. 31, 2014, Office Action, dated Jul. 17, 2015.
U.S. Appl. No. 14/222,364, filed Mar. 21, 2014, Office Action, dated Dec. 9, 2015.
U.S. Appl. No. 14/518,757, filed Oct. 20, 2014, Office Action, dated Dec. 1, 2015.
U.S. Appl. No. 13/835,688, filed Mar. 15, 2013, Final Office Action, dated Sep. 30, 2015.
U.S. Appl. No. 14/170,562, filed Jan. 31, 2014, Final Office Action, dated Sep. 25, 2014.

(56) References Cited

OTHER PUBLICATIONS

U.S. Appl. No. 13/949,043, filed Jul. 23, 2013, Office Action, dated Jul. 26, 2016.
U.S. Appl. No. 15/085,557, filed Mar. 30, 2016, First Office Action Interview, dated Jul. 1, 2016.
U.S. Appl. No. 14/449,083, filed Jul. 31, 2014, Final Office Action, dated Aug. 26, 2015.
U.S. Appl. No. 14/170,564, filed Jan. 31, 2014, Office Action, dated Jul. 25, 2015.
U.S. Appl. No. 14/170,566, filed Jan. 31, 2014, Office Action, dated Jul. 27, 2016.
U.S. Appl. No. 14/518,757, filed Oct. 20, 2014, Final Office Action, dated Jul. 20, 2015.
U.S. Appl. No. 14/170,565, filed Jan. 31, 2014, First Office Action Interview, dated Jul. 8, 2016.
U.S. Appl. No. 14/222,364, filed Mar. 21, 2014, Final Office Action, dated Jun. 24, 2016.
U.S. Appl. No. 14/533,433, filed Nov. 5, 2014, Office Action, dated Feb. 26, 2015.
U.S. Appl. No. 14/170,564, filed Jan. 31, 2014, Office Action, dated Dec. 4, 2017.
U.S. Appl. No. 13/949,043, filed Jul. 23, 2013, Office Action, dated May 7, 2015.
U.S. Appl. No. 13/949,043, filed Jul. 23, 2013, 1st Office Action Interview, dated Nov. 29, 2013.
U.S. Appl. No. 13/949,043, filed Jul. 23, 2013, 1st Office Action Interview, dated Oct. 15, 2013.
U.S. Appl. No. 15/050,658, filed Jan. 31, 2014, 1st Office Action Interview, dated Jun. 28, 2018.
U.S. Appl. No. 14/170,562, filed Jan. 31, 2014, Interview Summary, dated Nov. 28, 2014.
U.S. Appl. No. 14/170,562, filed Jan. 31, 2014, 1$^{st}$ Office Action Interview, dated Mar. 19, 2014.
U.S. Appl. No. 13/949,043, filed Jul. 23, 2013, Final Office Action, dated Feb. 24, 2014.
U.S. Appl. No. 14/975,697, filed Dec. 21, 2015, Final Office Action, dated Jan. 28, 2018.
U.S. Appl. No. 14/975,697, filed Dec. 21, 2015, Notice of Allowance, dated Mar. 21, 2019.
U.S. Appl. No. 14/975,697, filed Dec. 21, 2015, Office Action, dated Apr. 27, 2018.
Canese et al., "Chapter 2: PubMed: The Bibliographic Database," The NCBI Handbook, Oct. 2002, pp. 1-10.
Sirotkin et al., "Chapter 13: The Processing of Biological Sequence Data at NCBI," The NCBI Handbook, Oct. 2002, pp. 1-11.
Delcher et al., "Identifying Bacterial Genes and Endosymbiont DNA with Glimmer," BioInformatics, vol. 23, No. 6, 2007, pp. 673-679.
Mizrachi, Ilene, "Chapter 1: Gen Bank: The Nuckeotide Sequence Database," The NCBI Handbook, Oct. 2002, pp. 1-14.
Official Communication for Great Britain Patent Application No. 1404574.4 dated Dec. 18, 2014.
Kitts, Paul, "Chapter 14: Genome Assembly and Annotation Process," The NCBI Handbook, Oct. 2002, pp. 1-21.
"A Quick Guide to UniProtKB Swiss-Prot & TrEMBL," Sep. 2011, pp. 2.
"The FASTA Program Package," fasta-36.3.4, Mar. 25, 2011, pp. 29.
Kahan et al., "Annotea: an Open RDF Infrastructure for Shared Web Annotations", Computer Networks, Elsevier Science Publishers B.V., vol. 39, No. 5, dated Aug. 5, 2002, pp. 589-608.
POI Editor, "How To: Create Your Own Points of Interest," <http://www.poieditor.com/articles/how_to_create_your_own_points_of_interest/22 printed Jul. 22, 2012 in 4 pages.
Official Communication for Australian Patent Application No. 2014202442 dated Mar. 19, 2015.
Vivid Solutions, "JTS Topology Suite: Technical Specifications," <http://www.vividsolutions.com/jts/bin/JTS%20Technical%20Specs.pdf> Version 1.4, 2003, pp. 36.
Official Communication for European Patent Application No. 14187996.5 dated Feb. 12, 2015.
Official Communication for New Zealand Patent Application No. 628263 dated Aug. 12, 2014.
Palmas et al., "An Edge-Bunding Layout for Interactive Parallel Coordinates" 2014 IEEE Pacific Visualization Symposium, pp. 57-64.
Manske, "File Saving Dialogs," <http://www.mozilla.org/editor/ui_specs/FileSaveDialogs.html>, Jan. 20, 1999, pp. 7.
Murray, C., Oracle Spatial Developer's Guide—6 Coordinate Systems (Spatial Reference Systems), <http://docs.oracle.com/cd/B28359_01/appdev.111/b28400.pdf>, Jun. 2009.
Haralick et al., "Image Analysis Using Mathematical Morphology," Pattern Analysis and Machine Intelligence, IEEE Transactions, Jul. 1987, vol. PAMI-9, No. 4, pp. 532-550.
Huang et al., "Systematic and Integrative Analysis of Large Gene Lists Using DAVID Bioinformatics Resources," Nature Protocols, 4.1, 2008, 44-57.
Map Builder, "Rapid Mashup Development Tool for Google and Yahoo Maps!" <http://web.archive.org/web/20090626224734/http://www.mapbuilder.net/> printed Jul. 20, 2012 in 2 pages.
Gorr et al., "Crime Hot Spot Forecasting: Modeling and Comparative Evaluation", Grant 98-IJ-CX-K005, May 6, 2002, 37 pages.
Chen et al., "Bringing Order to the Web: Automatically Categorizing Search Results," CHI 2000, Proceedings of the SIGCHI conference on Human Factors in Computing Systems, Apr. 1-6, 2000, The Hague, The Netherlands, pp. 145-152.
Keylines.com, "An Introduction to KeyLines and Network Visualization," Mar. 2014, <http://keylines.com/wp-content/uploads/2014/03/KeyLines-White-Paper.pdf> downloaded May 12, 2014 in 8 pages.
Yang et al., "HTML Page Analysis Based on Visual Cues", A129, pp. 859-864, 2001.
Li et al., "Interactive Multimodal Visual Search on Mobile Device," IEEE Transactions on Multimedia, vol. 15, No. 3, Apr. 1, 2013, pp. 594-607.
Tangelder et al., "Freeform Shape Matching Using Minkowski Operations," The Netherlands, Jun. 1996, pp. 12.
VirusTotal—About, <http://www.virustotal.com/en/about/> Printed Jun. 30, 2014 in 8 pages.
Official Communication for Great Britain Patent Application No. 1411984.6 dated Dec. 22, 2014.
Official Communication for Australian Patent Application No. 2014210604 dated Jun. 5, 2015.
"HunchLab: Heat Map and Kernel Density Calculation for Crime Analysis," Azavea Journal, printed from www.azavea.com/blogs/newsletter/v4i4/kernel-density-capabilities-added-to-hunchlab/ on Sep. 9, 2014, 2 pages.
Reibel et al., "Areal Interpolation of Population Counts Using Pre-classi_ed Land Cover Data," Population Research and Policy Review, 2007, vol. 26, pp. 619-633.
Olanoff, Drew, "Deep Dive with the New Google Maps for Desktop with Google Earth Integration, It's More than Just a Utility," May 15, 2013, pp. 1-6, retrieved from the internet: http://web.archive.org/web/20130515230641/http://techcrunch.com/2013/05/15/deep-dive-with-the-new-google-maps-for-desktop-with-google-earth-integration-its-more-than-just-a-utility/.
Map of San Jose, CA. Retrieved Oct. 2, 2013 from http://maps.bing.com.
Griffith, Daniel A., "A Generalized Huff Model," Geographical Analysis, Apr. 1982, vol. 14, No. 2, pp. 135-144.
Official Communication for Australian Patent Application No. 2014213553 dated May 7, 2015.
Official Communication in New Zealand Application No. 628840 dated Aug. 28, 2014.
Celik, Tantek, "CSS Basic User Interface Module Level 3 (CSS3 UI)," Section 8 Resizing and Overflow, Jan. 17, 2012, retrieved from internet http://www.w3.org/TR/2012/WD-css3-ui-20120117/#resizing-amp-overflow retrieved on May 18, 2015.
Valentini et al., "Ensembles of Learning Machines", M. Marinaro and R. Tagliaferri (Eds.): WIRN VIETRI 2002, LNCS 2486, pp. 3-20.

(56) References Cited

OTHER PUBLICATIONS

Ananiev et al., "The New Modality API," http://web.archive.org/web/20061211011958/http://java.sun.com/developer/technicalArticles/J2SE/Desktop/javase6/modality/ Jan. 21, 2006, pp. 8.

Chung, Chin-Wan, "Dataplex: An Access to Heterogeneous Distributed Databases," Communications of the ACM, Association for Computing Machinery, Inc., vol. 33, No. 1, Jan. 1, 1990, pp. 70-80.

VB Forums, "Buffer A Polygon," Internet Citation, <http://www.vbforums.com/showthread.php?198436-Buffer-a-Polygon>, Specifically Thread #1, #5 & #11 retrieved on May 2, 2013, pp. 8.

"Potential Money Laundering Warning Signs," snapshot taken 2003, https://web.archive.org/web/20030816090055/http:/finsolinc.com/ANTI-MONEY%20LAUNDERING%20TRAINING%20GUIDES.pdf.

GIS-NET 3 Public _ Department of Regional Planning. Planning & Zoning Information for Unincorporated LA County. Retrieved Oct. 2, 2013 from http://gis.planning.lacounty.gov/GIS-NET3_Public/Viewer.html.

Official Communication for European Patent Application No. 14189802.3 dated May 11, 2015.

Official Communication for Great Britain Patent Application No. 1404573.6 dated Sep. 10, 2014.

Official Communication for Great Britain Application No. 1404457.2 dated Aug. 14, 2014.

Manno et al., "Introducing Collaboration in Single-user Applications through the Centralized Control Architecture," 2010, pp. 10.

Reddy et al., "Under the hood of GeoVRML 1.0," SRI International, Proceedings of the fifth symposium on Vurtual Reality Modeling Language (Web3D-VRML), New York, NY, Feb. 2000, pp. 23-28.

Official Communication for European Patent Application No. 14197895.7 dated Apr. 28, 2015.

"Andy Turner's GISRUK 2012 Notes" <https://docs.google.com/document/d/1cTmxg7mVx5gd89lqblCYvCEnHA4QAivH4l4WpyPsqE4/edit?pli=1> printed Sep. 16, 2013 in 15 pages.

Liu, Tianshun, "Combining GIS and the Huff Model to Analyze Suitable Locations for a New Asian Supermarket in the Minneapolis and St. Paul, Minnesota USA," Papers in Resource Analysis, 2012, vol. 14, pp. 8.

Pozzi et al., "Vegetation and Population Density in Urban and Suburban Areas in the U.S.A." Third International Symposium of Remote Sensing of Urban Areas Istanbul, Turkey, Jun. 2002, pp. 8.

Official Communication for New Zealand Patent Application No. 622517 dated Apr. 3, 2014.

Crosby et al., "Efficient Data Structures for Tamper-Evident Logging," Department of Computer Science, Rice University, 2009, pp. 17.

Keylines.com, "Visualizing Threats: Improved Cyber Security Through Network Visualization," Apr. 2014, <http://keylines.com/wp-content/uploads/2014/04/Visualizing-Threats1.pdf> downloaded May 12, 2014 in 10.

Keylines.com, "KeyLines Datasheet," Mar. 2014, <http://keylines.com/wp-content/uploads/2014/03/KeyLines-datasheet.pdf> downloaded May 12, 2014 in 2 pages.

Carver et al., "Real-Time Visibility Analysis and Rapid Viewshed Calculation Using a Voxel-Based Modelling Approach," GISRUK 2012 Conference, Apr. 11-13, Lancaster UK, Apr. 13, 2012, pp. 6.

Official Communication for New Zealand Patent Application No. 628495 dated Aug. 19, 2014.

Ghosh, P., "A Solution of Polygon Containment, Spatial Planning, and Other Related Problems Using Minkowski Operations," Computer Vision, Graphics, and Image Processing, 1990, vol. 49, pp. 1-35.

Umagandhi et al., "Search Query Recommendations Using Hybrid User Profile with Query Logs," International Journal of Computer Applications, vol. 80, No. 10, Oct. 1, 2013, pp. 7-18.

Official Communication for New Zealand Patent Application No. 622513 dated Apr. 3, 2014.

Hogue et al., "Thresher: Automating the Unwrapping of Semantic Content from the World Wide Web," 14th International Conference on World Wide Web, WWW 2005: Chiba, Japan, May 10-14, 2005, pp. 86-95.

Levine, N., "Crime Mapping and the Crimestat Program," Geographical Analysis, 2006, vol. 38, pp. 41-56.

Official Communication for European Patent Application No. 15179122.5 dated Nov. 9, 2015.

Official Communication for European Patent Application No. 14180432.8 dated Jun. 23, 2015.

Hibbert et al., "Prediction of Shopping Behavior Using a Huff Model Within a GIS Framework," Healthy Eating in Context, Mar. 18, 2011, pp. 16.

Microsoft Office—Visio, "Add and glue connectors with the Connector tool," <http://office.microsoft.com/en-us/visio-help/add-and-glue-connectors-with-the-connector-tool-HA010048532.aspx?CTT=1> printed Aug. 4, 2011 in 1 page.

SONRIS, "Using the Area of Interest Tools," <http://web.archive.org/web/20061001053327/http://sonris-www.dnr.state.la.us/gis/instruct_files/tutslide12> printed Jan. 3, 2013 in 1 page.

Official Communication for Great Britain Patent Application No. 1408025.3 dated Nov. 6, 2014.

"A First Look: Predicting Market Demand for Food Retail using a Huff Analysis," TRF Policy Solutions, Jul. 2012, pp. 30.

Official Communication for Australian Patent Application No. 2014201511 dated Feb. 27, 2015.

Wikipedia, "Ramer_Douglas_Peucker Algorithm," <http://en.wikipedia.org/wiki/Ramer%E2%80%93Douglas%E2%80%93Peucker_algorithm > printed Jul. 2011, pp. 3.

Official Communication for Great Britain Patent Application No. 1404457.2 dated Aug. 14, 2014.

Hansen et al., "Analyzing Social Media Networks with NodeXL: Insights from a Connected World", Chapter 4, pp. 53-67 and Chapter 10, pp. 143-164, published Sep. 2010.

AMNET, "5 Great Tools for Visualizing Your Twitter Followers," posted Aug. 4, 2010, http://www.amnetblog.com/component/content/article/115-5-grate-tools-for-visualizing-your-twitter-followers.html.

Notice of Acceptance for Australian Patent Application No. 2012216622 dated Jan. 6, 2015.

Hogue et al., "Thresher: Automating the Unwrapping of Semantic Content from the World Wide Web", 14th International Conference on World Wide Web, WWW 2005: Chiba, Japan, May 10-14, 2005.

Glaab et al., "EnrichNet: Network-Based Gene Set Enrichment Analysis," Bioinformatics 28.18 (2012): pp. i451-i457.

FireEye, <http://www.fireeye.com/> Printed Jun. 30, 2014 in 2 pages.

Official Communication for European Patent Application No. 14180142.3 dated Feb. 6, 2015.

Microsoft—Developer Network, "Getting Started with VBA in Word 2010," Apr. 2010, <http://msdn.microsoft.com/en-us/library/ff604039%28v=office.14%29.aspx> as printed Apr. 4, 2014 in 17 pages.

Bugzilla@Mozilla, "Bug 18726—[feature] Long-click means of invoking contextual menus not supported," http://bugzilla.mozilla.org/show_bug.cgi?id=18726 printed Jun. 13, 2013 in 11 pages.

Official Communication for European Patent Application No. 14199182.8 dated Mar. 13, 2015.

Official Communication for Netherlands Patent Application No. 2013306 dated Apr. 24, 2015.

Snyder, "Map Projections—A Working Manual," U.S. Geological Survey Professional paper 1395, United States Government Printing Office, Washington: 1987, pp. 11-21 and 60-70.

Dramowicz, Ela, "Retail Trade Area Analysis Using the Huff Model," Directions Magazine, Jul. 2, 2005 in 10 pages, http://www.directionsmag.com/articles/retail-trade-area-analysis-using-the-huff-model/123411.

Lee et al., "A Data Mining and CIDF Based Approach for Detecting Novel and Distributed Intrusions," Lecture Notes in Computer Science, vol. 1907 Nov. 11, 2000, pp. 49-65.

Qiu, Fang, "3d Analysis and Surface Modeling", <http://web.archive.org/web/20091202221925/http://www.utsa.edu/lrsg/Teaching/EES6513/08-3D.pdf> printed Sep. 16, 2013 in 26 pages.

(56) References Cited

OTHER PUBLICATIONS

Official Communication for European Patent Application No. 14158861.6 dated Jun. 16, 2014.
Ipbucker, C., "Inverse Transformation for Several Pseudo-cylindrical Map Projections Using Jacobian Matrix," ICCSA 2009, Part 1 LNCS 5592, pp. 553-564.
Official Communication for Australian Patent Application No. 2014210614 dated Jun. 5, 2015.
FireEye—Products and Solutions Overview, <http://www.fireeye.com/products-and-solutions> Printed Jun. 30, 2014 in 3 pages.
Official Communication for European Patent Application No. 14159464.8 dated Jul. 31, 2014.
Official Communication for European Patent Application No. 14191540.5 dated May 27, 2015.
Wongsuphasawat et al., "Visual Analytics for Transportation Incident Data Sets," Transportation Research Record 2138, 2009, pp. 135-145.
Rouse, Margaret, "OLAP Cube," <http://searchdatamanagement.techtarget.com/definition/OLAP-cube>, Apr. 28, 2012.
Goswami, Gautam, "Quite Writly Said!," One Brick at a Time, Aug. 21, 2005, pp. 7.
Official Communication for European Patent Application No. 14159464.8 dated Aug. 20, 2014.
Official Communication for Great Britain Patent Application No. 1413935.6 dated Jan. 27, 2015.
Official Communication for European Patent Application No. 14159464.8 dated Sep. 22, 2014.
Nierman, "Evaluating Structural Similarity in XML Documents", 6 pages, 2002.
Official Communication for Netherlands Patent Application No. 2012435 dated Jun. 4, 2014.
Definition "Identify", downloaded Jan. 22, 2015, 1 page.
Official Communication for Australian Patent Application No. 2014250678 dated Jun. 17, 2015.
Hardesty, "Privacy Challenges: Analysis: It's Surprisingly Easy to Identify Individuals from Credit-Card Metadata," MIT News on Campus and Around the World, MIT News Office, Jan. 29, 2015, 3 pages.
Rizzardi et al., "Interfacing U.S. Census Map Files with Statistical Graphics Software: Application and Use in Epidemiology," Statistics in Medicine, Oct. 1993, vol. 12, No. 19-20, pp. 1953-1964.
Official Communication for European Patent Application No. 14186225.0 dated Feb. 13, 2015.
Parks, D. et al. "Identifying biologically relevant differences between metagenomic communities." Bioinformatics 26.6 (2010): pp. 715-721.
Reibel, M., "Geographic Information Systems and Spatial Data Processing in Demography: a Review," Population Research and Policy Review, 2007, vol. 26, pp. 601-618.
Official Communication for New Zealand Patent Application No. 627962 dated Aug. 5, 2014.
"A Word About Banks and the Laundering of Drug Money," Aug. 18, 2012, http://www.golemxiv.co.uk/2012/08/a-word-about-banks-and-the-laundering-of-drug-money/.
Microsoft Office—Visio, "About connecting shapes," <http://office.microsoft.com/en-us/visio-help/about-connecting-shapes-HP085050369.aspx> printed Aug. 4, 2011 in 6 pages.
Mandagere, Nagapramod, "Buffer Operations in GIS," <http://www-users.cs.umn.edu/~npramod/enc_pdf.pdf> retrieved Jan. 28, 2010, pp. 7.
Official Communication for European Patent Application No. 14189344.6 dated Feb. 20, 2015.
Boyce, Jim, "Microsoft Outlook 2010 Inside Out," Aug. 1, 2010, retrieved from the internet https://capdtron.files.wordpress.com/2013/01/outlook-2010-inside_out.pdf.
Wikipedia, "Federated Database System," Sep. 7, 2013, retrieved from the internet on Jan. 27, 2015 http://en.wikipedia.org/w/index.php?title=Federated_database_system&oldid=571954221.
Map of San Jose, CA. Retrieved Oct. 2, 2013 from http://maps.yahoo.com.
Conner, Nancy, "Google Apps: The Missing Manual," May 1, 2008, pp. 15.
Open Street Map, "Amm's Diary:Unconnected ways and other data quality issues," http://www.openstreetmap.org/user/amm/diary printed Jul. 23, 2012 in 3 pages.
Baker et al., "The Development of a Common Enumeration of Vulnerabilities and Exposures," Presented at the Second International Workshop on Recent Advances in Intrusion Detection, Sep. 7-9, 1999, pp. 35.
Hur et al., "SciMiner: web-based literature mining tool for target identification and functional enrichment analysis," Bioinformatics 25.6 (2009): pp. 838-840.
Woodbridge, Stephen, "[geos-devel] Polygon simplification," <http://lists.osgeo.org/pipermail/geos-devel/2011-May/005210.html> dated May 8, 2011, pp. 3.
Huff et al., "Calibrating the Huff Model Using ArcGIS Business Analyst," ESRI, Sep. 2008, pp. 33.
Official Communication for New Zealand Patent Application No. 624557 dated May 14, 2014.
Acklen, Laura, "Absolute Beginner's Guide to Microsoft Word 2003," Dec. 24, 2003, pp. 15-18, 34-41, 308-316.
Official Communication for European Patent Application No. 14189347.9 dated Mar. 4, 2015.
Barnes et al., "Viewshed Analysis", GIS-ARC/INFO 2001, <www.evsc.virginia.edu/~jhp7e/evsc466/student_pres/Rounds.pdf>.
Official Communication for New Zealand Patent Application No. 628161 dated Aug. 25, 2014.
Huff, David L., "Parameter Estimation in the Huff Model," ESRI, ArcUser, Oct.-Dec. 2003, pp. 34-36.
Wikipedia, "Douglas_Peucker-Algorithms," <http://de.wikipedia.org/w/index.php?title=Douglas-Peucker-Algorithmus&oldid=91846042> printed Jul. 2011, pp. 2.
"Refresh CSS Ellipsis When Resizing Container—Stack Overflow," Jul. 31, 2013, retrieved from internet http://stackoverflow.com/questions/17964681/refresh-css-ellipsis-when-resizing-container, retrieved on May 18, 2015.
Official Communication for New Zealand Patent Application No. 628585 dated Aug. 26, 2014.
Bluttman et al., "Excel Formulas and Functions for Dummies," 2005, Wiley Publishing, Inc., pp. 280, 284-286.
Zheng et al., "GOEAST: a web-based software toolkit for Gene Ontology enrichment analysis," Nucleic acids research 36.suppl 2 (2008): pp. W385-W363.
Official Communication for New Zealand Patent Application No. 622272 dated Mar. 27, 2014.
Official Communication for European Patent Application No. 14180281.9 dated Jan. 26, 2015.
Map of San Jose, CA. Retrieved Oct. 2, 2013 from http://maps.google.com.
Sigrist, et al., "PROSITE, a Protein Domain Database for Functional Characterization and Annotation," Nucleic Acids Research, 2010, vol. 38, pp. D161-D166.
Madden, Tom, "Chapter 16: The BLAST Sequence Analysis Tool," The NCBI Handbook, Oct. 2002, pp. 1-15.
Official Communication for European Patent Application No. 15156004.2 dated Aug. 24, 2015.
Official Communication for European Patent Application No. 15179122.5 dated Sep. 11, 2015.
Definition "Overlay", downloaded Jan. 22, 2015, 1 page.
Official Communication for European Patent Application No. 14180321.3 dated Apr. 17, 2015.
Meystre et al., "Natural Language Processing to Extract Medical Problems from Electronic Clinical Documents: Performance Evaluation," Journal of Biomedical Informatics, vol. 39, No. 6, Dec. 1, 2006, pp. 589-599.
Heinze et al., "LifeCode (TM)—A Natural Language Processing System for Medical Coding and Data Mining," AAAI/IAAI 2000, Jul. 30, 2000, pp. 965-972.
Official Communication for European Patent Application No. 14197879.1 dated Apr. 28, 2015.
Ohno-Machado, Lucila "Realizing the Full Potential of Electronic Health Records: The Role of Natural Language Processing," Journal of the American Medical Informatics.

(56) References Cited

OTHER PUBLICATIONS

Hazlehurst et al., "Natural Language Processing in the Electronic Medical Record," American Journal of Preventive Medicine, vol. 29, No. 5, Dec. 1, 2005, pp. 434-439.

Official Communication for European Patent Application No. 15179122.5 dated Jul. 10, 2017.

Androutsopoulos et al., "Natural Language Interfaces to Databases—An Introduction," Journal of Natural Language Engineering, Mar. 16, 1995, retrieved from the internet http://pdf.aminer.org/000/815/187/natural_language_interfaces_to_databases_an_introduction.pdf, retrieved on Jul. 9, 2014.

Hahn et al., "medSynDiKATe—a Natural Language System for the Extraction of Medical Information from Findings Reports," International Journal of Medical Informat, vol. 67, No. 1-3, Dec. 4, 2002, pp. 63-74.

\* cited by examiner

FIG. 5C

MEDICAL CLAIMS LEAD SUMMARY REPORT GENERATION

BENEFIT CLAIM

This application claims the benefit 35 U.S.C. § 120 as a continuation of application Ser. No. 14/975,967, filed Dec. 21, 2015, which claims the benefit under 35 U.S.C. § 119(e) of provisional application 62/099,082, filed Dec. 31, 2014, the entire contents of which are hereby incorporated by reference for all purposes as if fully set forth herein. Applicants hereby rescind any prior disclaimer of claim scope and advise the USPTO that the present claims may be broader than in the parent applications.

TECHNICAL FIELD

The present disclosure relates to data processing techniques for fraud detection in the context of health insurance.

BACKGROUND

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

Healthcare fraud accounts for an estimated $60-80 billion dollars/year in waste. Some estimate that the damages constitute 3-10% of all healthcare expenditures. One source of fraud is prescription drug fraud. Examples of prescription fraud include forging prescriptions, altering prescriptions, stealing prescription pads, calling in prescriptions or using online pharmacies, doctor/pharmacy shopping (for example, going to multiple doctors, emergency rooms, or pharmacies and seeking prescriptions while faking symptoms such as migraine headaches, toothaches, cancer, psychiatric disorders, and attention deficit disorder, or having deliberately injured oneself), going across state lines to seek fulfillment at multiple pharmacies, refilling prescriptions before ninety days, and so forth. Prescription fraud primarily occurs at retailer pharmacies, and primarily with narcotics, anti-anxiety medications, muscle relaxants, and hypnotics.

Other sources of fraud include insurance claims fraud such as a provider charging more than peers for services, a provider billing for more tests per patient than peers, a provider billing for unlikely or unnecessary medical procedures, upcoding of services or billing for the most expensive of options, upcoding of equipment or billing for a more expensive item and delivering a lower cost item, consistently billing for high cost medical equipment, such as Durable Medical Equipment, billing for procedures or services not provided, filing duplicate claims that bill for the same service on two separate occasions, unbundling a group of services so that the services billed one at a time yield more compensation than if they had been bundled together, kickbacks from referrals, transportation fraud, collecting money from multiple insurance providers, using surgical modifiers to increase reimbursement, fraud involving viatical health and life insurance, nursing home fraud such as lack of services rendered or services rendered by non-licensed professionals, and so forth.

Prescription claims, doctor office claims, medical procedure claims, hospital claims, medical equipment claims, and other medical claims (collectively referred to as medical claims or healthcare claims) may number in the millions or billions per year. And each medical claim may include numerous types of data, such as billing codes, patient identifier, location, service provider identifier, service date, and the like. Thus, while databases of medical claims contain vast amount of information, selectively mining the available information for useful purposes is not a trivial task.

Techniques for detecting medical claims fraud may include automated and manual processes. For example, although potentially fraudulent medical claims (referred to as fraud leads) can be identified using automated techniques, whether or not to take further action on particular ones of the fraud leads (e.g., investigate, deny reimbursement, notify authorities, pursue remedial action, hold for additional available information, etc.) may require human analysis and decision-making. When provided with a list of fraud leads, however, persons (referred to as fraud analysts) tasked with analyzing or vetting these identified leads may be overwhelmed by the large number of leads in the list. Lists may also lack context and/or useful information for fraud analysts to make an accurate and/or efficient assessment about whether to take further action on particular ones of the identified leads.

SUMMARY OF THE INVENTION

The appended claims may serve to summarize the invention.

BRIEF DESCRIPTION OF THE DRAWINGS

In the drawings:

FIG. 5A, FIG. 5B, FIG. 5C illustrate another example lead summary report according to some embodiments.

DETAILED DESCRIPTION

Figure 1:
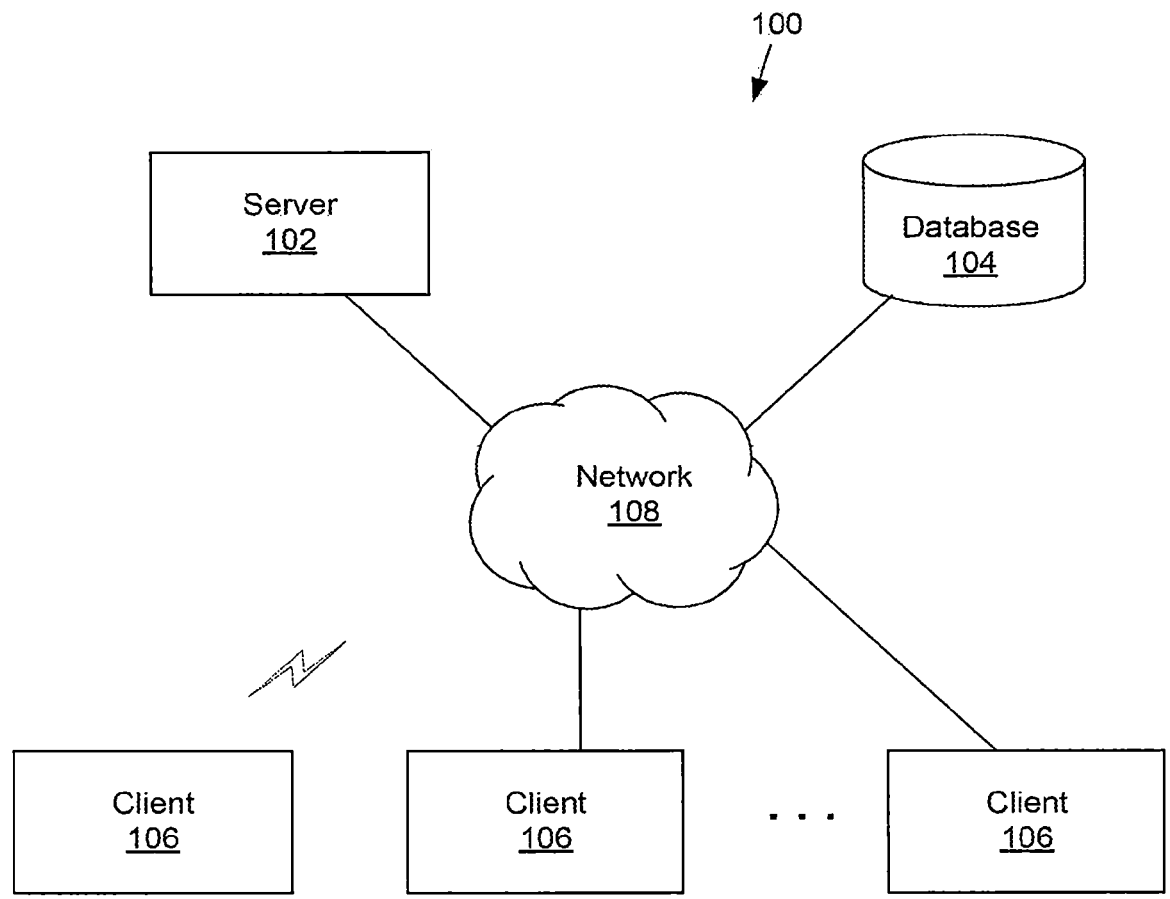
FIG. 1 illustrates an example computer system that may be programmed for automatically generating lead summary reports according to some embodiments.

In the following description, for the purposes of explanation, numerous specific details are set forth in order to provide a thorough understanding of the present disclosure. It will be apparent, however, that the present disclosure may be practiced without these specific details. In other instances, well-known structures and devices are shown in block diagram form in order to avoid unnecessarily obscuring the present disclosure.

Embodiments are described in sections according to the following outline:

1.0 GENERAL OVERVIEW
2.0 STRUCTURAL OVERVIEW
3.0 FUNCTIONAL OVERVIEW 4.0 IMPLEMENTATION EXAMPLE—DATA STRUCTURES 5.0 IMPLEMENTATION EXAMPLE—HARDWARE OVERVIEW 1.0 General Overview In an embodiment, a computer-implemented method comprises, in response to receiving lead data identifying an entity associated with a health care claim relating to suspected fraud, determining one or more data sources that were used to identify the entity or the suspected fraud; determining a subset of a plurality of data display elements, based on the determined one or more data sources, wherein each of the plurality of data display elements is configured to cause displaying health care claims data associated with the entity in a designated format; automatically obtaining, from a data repository, specific health care claims data associated with the entity for each of the plurality of data display elements in the subset; generating a lead summary report associated with the entity using a report template, the subset, and the obtained specific health care claims data. Each of the features of the method is performed using one or more computing devices or processors.

In another embodiment, a computer system comprises one or more databases including a plurality of health care claims data and a plurality of data display elements; a report generator component, at least partially implemented by computing hardware, determines, in response to suspected fraud by an entity associated with a health care claim, which one or more sources were used to identify the suspected fraud, determines a subset from among the plurality of data display elements, from the one or more databases, based on the determined one or more sources, automatically obtain specific health care claims data associated with the entity, from the one or more databases, for each of the plurality of data display elements in the subset, dynamically generate a lead summary report associated with the entity using a report template, the subset, and the obtained specific health care claims data; wherein each of the plurality of data display elements is configured to display specific health care claims data associated with the entity in a specific format; a user interface component, at least partially implemented by computing hardware, automatically provides the lead summary report to facilitate assessment of the suspected fraud by a user.

2.0 Structural Overview

Techniques are described herein for automatically and dynamically generating a lead summary report corresponding to a potential fraudulent lead identified using one or more fraud detection models or schemes. Thus a lead, in an embodiment, is a digitally stored dataset indicating suspected fraud and may be associated in various embodiments with a person or entity, a data source, and/or a fraud detection model or scheme that resulted in identifying the lead. In an embodiment, a programmed method or algorithm enables a lead, identified by the same party or a third party with respect to the party using the method or algorithm to be intelligently presented, using computer-implemented presentation, to persons responsible for assessing the identified lead to determine whether to pursue the lead for anti-fraud purposes.

In an embodiment, a plurality of specific types of data relating to the identified lead (for example, medical claims data associated with the identified lead) are automatically accessed, collated, and presented in computer-based formats that are conducive to ready comprehension (for example, table over graphical format, graphical over table or text format, etc.) in the lead summary report. Each of the plurality of specific types of data is selected to show evidence of suspected fraud, to provide context in which the suspected fraud was detected, and/or to anticipate and reduce/eliminate data gathering and collation that persons assessing the identified lead are likely to perform to effectively assess the identified lead. The plurality of specific types of data, which may be displayed using widgets, may be lead-specific and/or specific to a particular fraud detection model or scheme. In an embodiment, systems and techniques further permit persons to add to the lead summary report, create derivative documents or items based on the lead summary report, and/or provide information to improve future lead summary reports. Among other aspects, systems and techniques monitor activity taken on the lead summary report to improve the selection of certain ones of the specific types of data and the display format of the specific types of data to be included in lead summary reports.

Various modifications to the embodiments will be readily apparent to those skilled in the art, and principles defined herein may be applied to other embodiments and applications without departing from the spirit and scope of the invention. Moreover, in the following description, numerous details are set forth for the purpose of explanation. However, one of ordinary skill in the art will realize that embodiments of the invention may be practiced without the use of these specific details. In other instances, well-known structures and processes are not shown in block diagram form in order not to obscure the description of the invention with unnecessary detail. Thus, the present disclosure is not intended to be limited to the embodiments shown, but is to be accorded the widest scope consistent with the principles and features disclosed herein.

FIG. 1 illustrates an example computer system 100 in which the techniques described may be practiced, according to some embodiments. System 100 is a computer-based system. The various components of system 100 are implemented at least partially by hardware at one or more computing devices, such as one or more hardware processors executing instructions stored in one or more memories for performing various functions described herein. System 100 illustrates only one of many possible arrangements of components configured to perform the functionality described herein. Other arrangements may include fewer or different components, and the division of work between the components may vary depending on the arrangement.

System 100 includes a server 102, a database 104, one or more clients 106, and a network 108. Each of the server 102, database 104, and clients 106 is in wired or wireless communication with the network 108.

Server 102 comprises one or more servers, computers, processors, database servers, and/or computing devices that are programmed or configured to communicate with the database 104 and/or clients 106 via network 108. The server 102 is programmed or configured to automatically assess medical claims data stored in database 104 for the purpose of detecting suspected fraud. Server 102 hosts one or more applications, websites, or other visual or user interface mechanisms related to use of medical claims data as described in detail below. Server 102 may be located at one or more geographically distributed locations. Although one server 102 is shown in FIG. 1, system 100 may, depending on the embodiment, comprise one, two, or any number of servers 102, which may work alone and/or collectively to provide the functionality described herein.

Database 104 comprises one or more data repositories, databases or storage devices that are programmed or configured to store and maintain medical claims data, data associated with medical claims data, data associated with fraud detection or fraud detection lead generation, data associated with presentation of fraud detection lead-related data, data associated with users of medical claims data, and/or instructions for use by server 102 and/or clients 106 as described herein. Database 104 may, in some embodiments, be located at one or more geographically distributed location relative to server 102. Server 102 and/or clients 106 may, in some embodiments, access database 104 via network 108. Alternatively, server 102 may access database 104 without needing network 108. As another alternative, database 104 may be included within server 102. System 100 may, depending on the embodiment, comprise one, two, or any number of databases 104 configured to individually and/or collectively store the data described herein.

Clients 106 comprise computing devices, including but not limited to, work stations, personal computers, general purpose computers, laptops, Internet appliances, hand-held devices, wireless devices, wired devices, portable devices, wearable computers, cellular or mobile phones, portable digital assistants (PDAs), smart phones, tablets, multi-processor systems, microprocessor-based or programmable consumer electronics, game consoles, set-top boxes, network PCs, mini-computers, and the like. Each of the clients 106 includes applications, software, and/or other executable instructions to facilitate various aspects of the medical claim fraud detection techniques described herein. Clients 106 may also include additional applications or other interface capabilities to communicate with the server 102 and/or database 104. Clients 106 may, depending on the embodiment, be located geographically dispersed from each other. Although three clients 106 are shown in FIG. 1, more or less than three clients 106 may be included in system 100. Clients 106 are also referred to as devices, requesting devices, requesting clients, requesting machines, requestors, and the like.

Network 108 comprises one or more data communications networks including any of one or more of a local area network (LAN), a wireless LAN (WLAN), a wide area network (WAN), a wireless WAN (WWAN), a metropolitan area network (MAN), an ad hoc network, an intranet, an extranet, a virtual private network (VPN), an internetwork, a portion of a public switched telephone network (PSTN), a cellular network, or a combination of two or more such networks. When network 108 comprises a public network, security features (for example, VPN/SSL secure transport) may be included to ensure authorized access within system 100.

Figure 2:
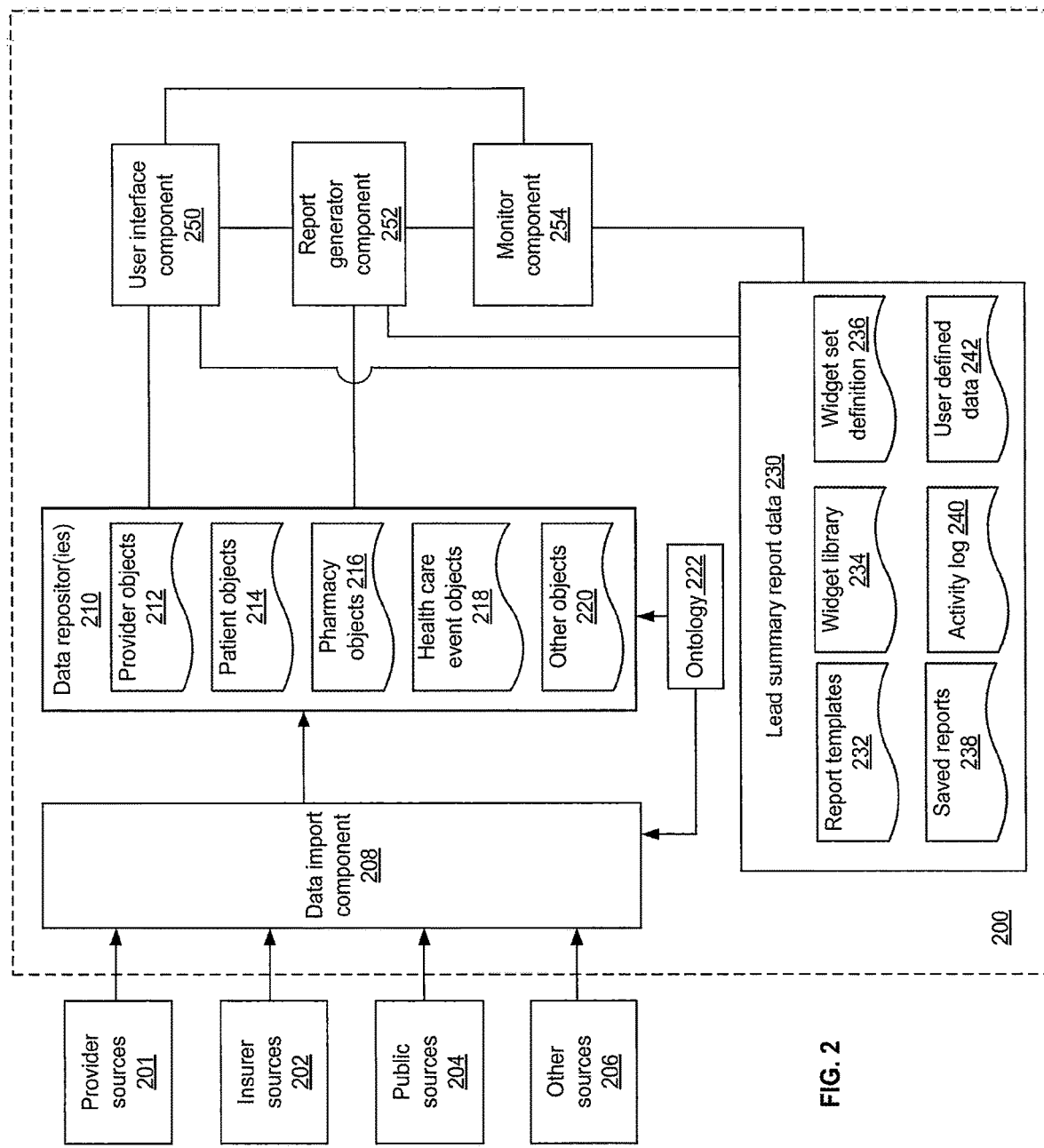
FIG. 2 illustrates example additional details of the computer system of FIG. 1 according to some embodiments.

FIG. 2 illustrates a computer system comprising various example objects and components that may be utilized to perform fraud lead summary report generation and presentation, according to some embodiments.

System 200 is a computer-based system. The various components of system 200 are implemented at least partially by hardware at one or more computing devices, such as one or more hardware processors executing instructions stored in one or more memories for performing various functions described herein. The components are communicatively coupled (for example, via appropriate interfaces) to each other and to various data sources, so as to allow information to be passed between the components and/or to share and access common data. System 200 illustrates only one of many possible arrangements of components configured to perform the functionality described herein. Other arrangements may include fewer or different components, and the division of work between the components may vary depending on the arrangement. In an embodiment, system 200 is implemented by one or more of the computer systems 100 and/or 700 described herein.

System 200 comprises a data import component 208 that is configured or programmed to collect data from a variety of sources, including one or more of provider sources 201, insurer sources 202, public sources 204, and/or other sources 206 as described herein. The data may be collected from each included source 201-206 on one or on multiple occasions, depending on factors such as the size of the data source, the accessibility of the data source, and how frequently the data source changes. Depending on the form in which the data is collected, the data import component 208 may optionally be configured or programmed to perform Extract, Transform, and Load ("ETL") operations on the collected data to generate objects that conform to one or more defined ontologies 222. Ontologies 222 may be, for example, dynamic ontologies, static schemas, and/or other data structure definitions.

The data import component 208 is configured or programmed to cause the collected data to be stored in one or more repositories of data 210. The one or more repositories of data 210 may store, among other object types, some or all of: provider objects 212, patient objects 214, pharmacy objects 216, health care event objects 218, and/or other objects 220, each of which corresponds to a different discrete object type defined by the one or more ontologies 222. Other objects 220 may include any category of object type deemed desirable. For example, another object type may be administrative event objects. Thus, in an embodiment, data obtained from healthcare providers, insurers, public sources, and other sources may be represented in computer storage using object-oriented data representation techniques to represent providers, patients, pharmacies, events, and other items as objects that may be selectively queried to identify real-world relationships, events, or transactions suspected of fraud. "Object," in this context, may refer to a digitally stored data element such as a programmatic object that is instantiated and managed using an object-oriented application program.

Repositories 210 may be included in, for example, the database(s) 104. Repositories 210 may be collectively referred to as a medical claims repository. Examples of repositories 210 and corresponding objects 212-220 are described in subsequent sections. In some embodiments, some or all of the contents of repositories 210 may be organized as relational data instead of or in addition to object-oriented representations.

System 200 also includes one or more instances of lead summary report data 230. The one or more lead summary report data 230 may store, among other object types, report templates 232, widget library 234, widget set definition 236, saved reports 238, activity log 240, user defined data 242, and/or other data. Each of these may be utilized to dynamically and automatically generate summary reports corresponding to potential medical claim fraud leads that are identified using one or more fraud detection models to users (for example, fraud analysts) of system 200.

Report templates 232 comprise one or more lead summary report templates that define the layout, format, data positions, content type, and other presentation aspects of lead summary reports to be generated for each of the identified leads. For example, the report templates 232 may comprise web page templates. Report templates 232 may also be referred to as a report template library.

Widget library 234 comprises a plurality of widgets, each of the widgets associated with a particular type or category of lead information to be obtained from the data repositories 210 and formatted in a certain way for presentation in a lead summary report. In some embodiments, the plurality of widgets may be considered to be templates to be embedded in a report template, data display elements, content type display or presentation elements, or content category display or presentation elements. A lead summary report, to be discussed in detail below, is generated using at least one lead summary report template from the report templates 232. And the lead summary report, in turn, is populated by one or more widgets.

Widget set definition 236 comprises definitions, mappings, or correlations of which widgets should be presented together in a lead summary report for a given identified potential lead. In an embodiment, particular one or more widgets (for example, a widget set) may be mapped to a particular fraud detection model. Each of a plurality of fraud detection models may have a particular set of widgets associated therewith. A default set of widgets may also be defined for cases where the fraud detection model(s) associated with a lead is unknown. Fraud detection models comprise techniques (based on statistics, feedback, known fraud schemes, etc.) used to identify potential fraudulent medical claims leads and may be implemented using computer programs, subroutines, functions, processes, methods, objects or other software elements, which may be uniquely identified by a model or scheme name.

Saved reports 238 comprise lead summary reports that are stored after their creation. Updates or any changes to existing lead summary reports are also saved to saved reports 238. For each saved lead summary report, associated information such as the date and time stamp, version information, and other housekeeping information may also be stored in the saved reports 238. Activity log 240 comprises a log of activity associated with each of the lead summary reports saved in the saved reports 238. Activity can include user navigation, user input, access times, access duration, and any other user interaction information that is tracked, monitored, and/or captured associated with a given lead summary report. Data in the activity log 240 may be used as feedback data to refine future lead summary reports, widgets, presentation format of data in a given widget, and the like. User defined data 242 comprises documentation or other information that may be expressly created by a user based on a given lead summary report. For example, a user may actuate a button in a lead summary report to "freeze" the lead summary report at a particular point in time to serve as an evidentiary document for later use. The "frozen" lead summary report is a snapshot or screenshot of the report at that point in time, and may be saved as a separate evidentiary document or item from the original lead summary report. As discussed in detail below, the original lead summary report is continually or periodically updated as new data becomes available.

System 200 also includes a user interface component 250 that is configured or programmed to provide a graphical user interface (GUI) to present information to and receive inputs from a user, such as a fraud analyst, investigator, etc., at one of the clients 106. Information presented to the user may include, without limitation, an interface to trigger dynamic generation of a lead summary report, lead summary reports, follow-on pages/windows provided by lead summary reports, and the like. Inputs received from a user may include, without limitation, a lead identifier to trigger lead summary report generation, navigation requests within the lead summary report, user request to "freeze" a lead summary report, input of notes and comments in a notes field of the lead summary report, user request for follow-on information via actuation of hyperlinks, mouse-overs, and the like.

Report generator component 252 is configured or programmed for creating a lead summary report for a given lead. Report generator component 252 interfaces with lead summary report data 230 and user interface component 250 to create a report. Among other things, a particular report template is obtained from the report templates 232. A particular set of widgets, as specified by the widget set definition 236, is obtained from the widget library 234 to populate the report. Each of the widgets in the particular set of widgets, in turn, obtains particular type of data associated with the lead stored in the data repositories 210. Together, particular lead-related data is presented in a particular format and style in the lead summary report to facilitate user analysis of the lead to determine whether to and/or how to pursue the lead. When any of the particular lead-related data included in the lead summary report changes (for example, new medical claims are submitted for reimbursement by the lead, address change is submitted), report generator component 252 updates the lead summary report accordingly. The updates may occur continually, periodically, in real-time, or approximately in real-time. Report generator component 252 interfaces with saved reports 238 to store the original and updated versions of the lead summary report.

Monitor component 254, in coordination with the user interface component 250, configured or programmed to track, detect, or monitors user interaction, activity, navigation, or actions taken on the lead summary report by the user. Detected user interaction, activity, navigation, or actions are stored in the activity log 240. Where the user creates new documents or items from the lead summary report, as discussed above, monitor component 254 may facilitate such creation and storage in the user defined data 242.

In one embodiment, components 250, 252, 254 comprise one or more software components, programs, applications, or other units of code base or instructions configured to be executed by one or more processors included in the server 102 of system 100. In other embodiments, the functionalities or operations of one or more of components 250-254 is handled by one or more clients 106, or shared between one or more servers 102 and one or more clients 106. As an example, the functionalities of the user interface component 250 may be provided by a client 106, while those of components 252-254 are provided by the server 102. Although components 250-254 are depicted as distinct components in FIG. 2, components 250-254 may be implemented as fewer or more components than illustrated. Any of components 250-254 may communicate directly or over a network with one or more devices included in the system 100, such as server 102, database 104, or clients 106, as needed to implement the functionality described herein.

3.0 Functional Overview

In an embodiment, the data objects and components depicted in FIG. 2 are used at various points of a workflow for identifying suspected fraud. The workflow may comprise a plurality of stages and in one embodiment a first stage is lead generation. The lead generation stage involves identifying suspected cases or records of health care fraud for further investigation. A lead, as described herein, is a dataset comprising one or more electronic or digital data items that are stored, at least transiently, in computer memory or storage and that identify a particular individual, organization, or event that is suspected as consisting of, relating to, or indicating actual or possible fraud, or is at an increased probability for consisting of, relating to, or indicating fraud.

The term lead may also be used herein to refer to a digital data object that represents the suspicious individual, organization, or event.

One way to identify leads is to receive tips concerning potentially fraudulent activities. A tip may come from a person or entity. An "entity," in this disclosure, may be a patient, doctor, other healthcare provider or other person, or an institution such as an insurer, HMO, hospital, clinic, medical practice group, or any other form of legal entity. Another way to identify leads is to review networks of individuals and/or organizations connected to instances of fraud described in media reports, indictments, or other publications. Another way to identify leads is to apply business rules to the various data objects and relationships described herein to flag potentially fraudulent activity, such as a male receiving treatment for ovarian cancer. Another way to identify leads is to identify outliers or other noticeable patterns outside the norm based on existing knowledge of healthcare consumption. Data objects associated with unusual values for these metrics may be investigated as leads.

Figure 3:
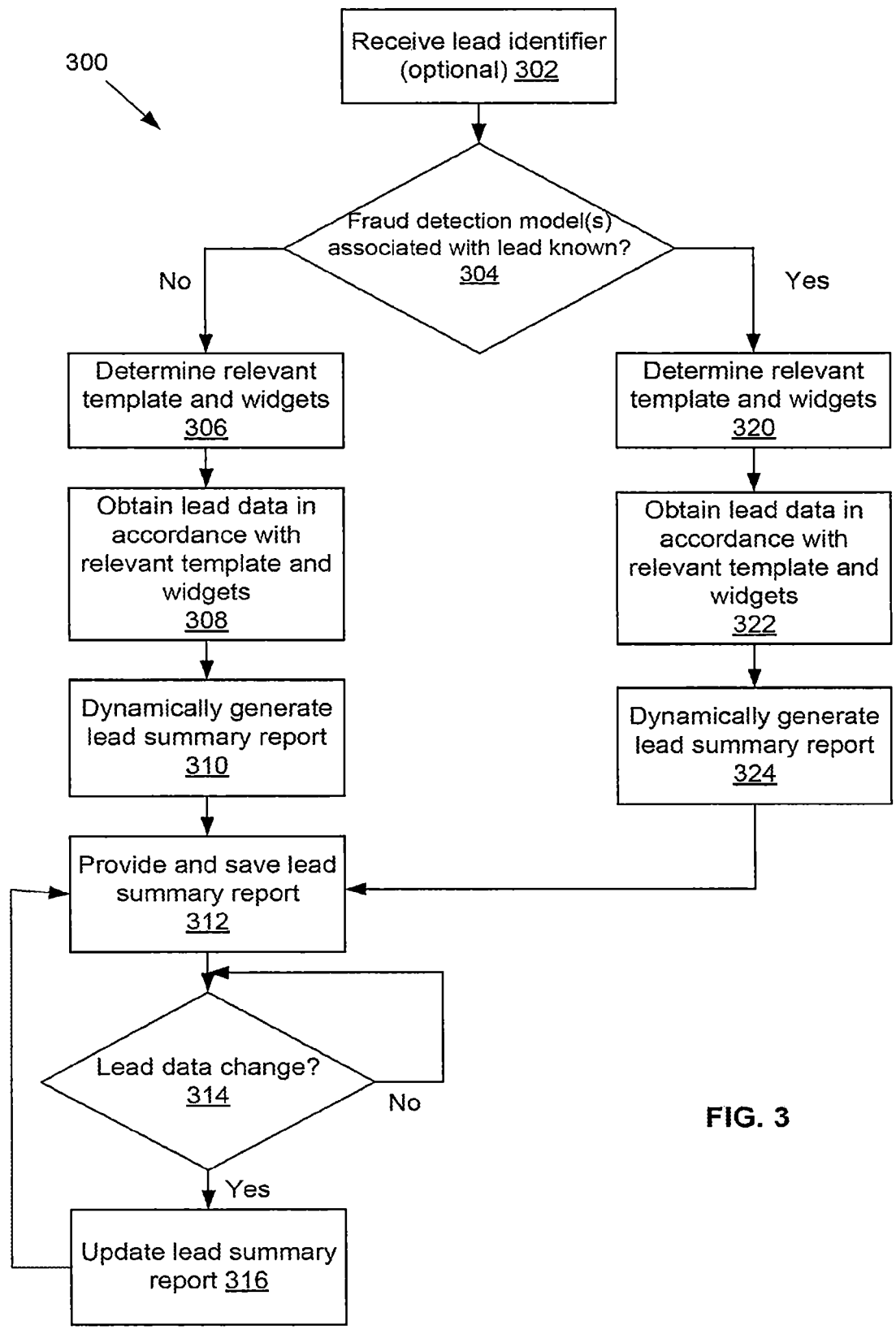
FIG. 3 illustrates an example flow or algorithm that may be programmed to dynamically generate lead summary reports according to some embodiments.

FIG. 3 illustrates an example flow or algorithm that may be programmed for dynamically generating lead summary reports, according to some embodiments. In an embodiment, each of the processes described in connection with the functional blocks of FIG. 3 may be implemented using one or more computer programs, other software elements, and/or digital logic in any of a general-purpose computer or a special-purpose computer, while performing data retrieval, transformation and storage operations that involve interacting with and transforming the physical state of memory of the computer. The flow 300 of FIG. 3 is described below in conjunction with the objects and components of FIG. 2, according to an embodiment, for purposes of illustrating a clear example. Flow 300 depicts example techniques for generating a lead summary report corresponding to a particular identified lead. The process of flow 300 may be repeated for each of the other identified leads to generate respective lead summary reports.

In block 302, the user interface component 250 presents a graphical user interface (GUI) for initiating generation of a lead summary report. A user, such as a fraud analyst, may input an identifier of a potential fraud lead into a search field or the like to initiate generation of a lead summary report corresponding to such lead. User interface component 250 receives a lead identifier in response. Examples of lead identifiers include, without limitation, a provider identification number (PIN), a tax identification number (TIN) associated with the lead, lead name (for example, provider name, address, phone number, etc.), and/or other unique identifying information sufficient to access medical claims data corresponding to the lead in a data store, such as data repositories 210. In an example, the user may have a list of potential fraud leads that were identified by lead generation techniques. The list of potential fraud leads may include hundreds or thousands of leads, with each lead identified by a PIN.

Alternatively, if identifiers of potential fraud leads are known to system 100 or 200, then block 302 may be optional. For example, system 100 or 200 may already interface with another system that performed the lead generation, or the identified leads are automatically communicated to system 100 or 200.

At block 304, the report generator component 252 is configured or programmed to determine whether the particular identified lead is associated with one or more particular fraud detection models. The particular identified lead is generated or becomes known based on one or more fraud detection models (also referred to as fraud schemes or fraud detection techniques). However, the particular fraud detection model(s) that identified or generated that particular identified lead may not be known by system 100, 200.

For example, if the user manually entered the particular identified lead in block 302 (from a list of leads), the source(s) from which the particular identified lead was generated may not be known. Conversely, if the particular identified lead is generated by the same system that generates the lead summary report, or the system that surfaced the particular identified lead communicated the fraud detection model(s) associated with that lead to the lead summary report system, then the particular fraud detection model(s) used to find the particular identified lead may be known. Examples of fraud detection models or techniques include, without limitation: amounts paid outlier, phantom provider, medical unit outlier, improbable sequencing, unbundling, sober living and drug screening, member overlap, indiscriminate billing, network, tips, upcoding, classification or pattern matching, and/or a variety of other fraud detection models or techniques.

If the fraud detection model(s) associated with the particular identified lead is not known (no branch of block 304), then report generator component 252 is configured or programmed to determine the relevant template and widgets for the particular identified lead in block 306. Report generator component 252 is configured or programmed to access at least widget set definition 236 to look-up the template and widgets corresponding to the case where the source (for example, fraud detection model(s)) of the particular identified lead is not known. In an embodiment, a particular template may be associated with a particular set of widgets, a particular template may be associated with more than one set of widgets, templates may be associated with fraud detection models independent of widgets and any one or more widgets may be included in any template, a single template may be defined for the unknown source case and one or more templates (which may be the same or different from the unknown source template) may be defined for the known source case, and/or a single template may be used for known and unknown sources with a particular widget set defined for each of the unknown source, source 1, source 2, source 3, and the like.

Widgets that may be included in a lead summary report, in which the lead summary report's overall layout and format are defined by a report template, comprise without limitation:

Biographical or basic provider information—PIN, TIN, name, address, phone, specialization, potential total reimbursement amount (also referred to as total exposure), etc.

Notes and comments—notes and/or comments about the particular identified lead provided by the lead generator, input field for user notes and comments based on review of lead summary report Paid to TIN—amounts paid to a particular TIN per year Address view (map)—map showing where the provider is located Top procedure (CPT) codes—top procedure codes, number of claims per code, amount billed per code, amount paid out (reimbursed) per code, etc.

Member overlap visualization (also referred to as network)—extent of shared members, shared providers, and/or shared commonality between the provider and others Code breakdown or distribution—visualization of billing distribution across (top) procedure codes for provider and comparison against other providers (may further breakdown by specialty and/or region)

Same date of service—amount billed per day

Statistics—shows various statistics about the provider relative to other related providers such as, as examples and without limitation, number of units per procedure per member per month, amount charged per unit, number of units per member, total amounts, number of unique procedures relative to all procedures by specialty, region, and units of procedures User feedback—present a set of feedback choices; alternatively, may be included in the Notes and comments widget Other types of lead-related data to display in a specific format.

Widgets comprise stand-alone applications, display elements, or other visualization mechanisms that may be embedded into other applications or documents (for example, templates for web pages). Each widget, in turn, is able to obtain and format specific data in accordance with the display requirements specified in the widget. For example, one widget may be configured to display a bar graph of amounts billed per year per procedure code billed by the provider, a second widget may be configured to display a two-dimensional map pinpointing a certain location therein, and a third widget may be configured to display a table of top procedure codes with corresponding number of claims, amount billed, and amount paid out. In an embodiment, the report templates 232 may comprise templates for web pages, JSON blobs that can be populated for use in electronic responses to other systems, or other instructions for formatting electronic documents.

In an embodiment, the widget set definition 236 can specify an unknown source report template and a default set of widgets when the source is not known (also referred to as an unknown source widget set or default widget set). The default widget set comprises a subset of the possible widgets. The default widget set comprises, for example, the following widgets: biographical or basic provider information, notes and comments, two-dimensional map, paid to TIN, top procedure codes, code breakdown, network, and statistics.

In block 308, report generator component 252 is configured or programmed to obtain lead data (also referred to as lead-related data) from data repositories 210 in accordance with the default widget set for the particular identified lead. Any data required by the default template may also be obtained at this time (for example, which analyst is assigned to review the lead summary report). The default template and default widget set are respectively accessed from report templates 232 and widget library 234 to facilitate data acquisition.

In block 310, report generator component 252 is configured or programmed to dynamically generate a lead summary report for the particular identified lead using the default template, default widget set, obtained lead data, and any other relevant data. The lead summary report is dynamically generated in real-time or near real-time, meaning that the report is generated without a significant time delay with respect to other steps in the flow of FIG. 3, and based upon then-current data in the data repositories; further, after the report is generated at block 324, flow proceeds promptly to other blocks of the flow to facilitate prompt output of the report to a computer display device or other output device.

In an embodiment, the lead summary report automatically brings together relevant information about the particular identified lead for an analyst to review and make a decision about next steps regarding the particular identified lead (for example, pay reimbursement request, reject reimbursement request, flag as fraudulent, forward to an investigator, input notes to continue review, etc.). The lead summary report also serves as a continual reference point for multiple users/viewers that may review and analyze the fraud potential of the particular identified lead, such as by including notes and comments capture. For example, a particular report may go back and forth and/or traverse different stages of fraud analysis and may be reviewed at different points in time by one or more of each of analysts, team leaders, investigators, triagers, and the like. Lead summary reports are discussed in greater detail below in conjunction with FIG. 4, FIG. 5A, FIG. 5B, FIG. 5C. In some embodiments, lead summary reports for a plurality of identified leads may be generated in batch.

In block 312, user interface component 250, in conjunction with report generator component 252, is configured or programmed to facilitate presentation of the lead summary report generated in block 310. The lead summary report may be provided to one or more devices for presentation. For example, the lead summary report may be provided to a client 106 for display using a computer display device coupled to the client, or transmitted to another computer system using electronic messaging, or printed, or communicated programmatically to another application, program or system.

In an embodiment, the report generator component 252 is configured or programmed to save the lead summary report in saved reports 238.

Once a lead summary report has been created, the report generator component 252 is configured or programmed to continually or periodically monitor whether any lead data used in the lead summary report changes in data repositories 210 in block 314. For example, lead data change includes, without limitation, provider address change or new medical claims submissions by the provider associated with the particular identified lead. If there is no data change (no branch of block 314), then report generator component 252 is configured or programmed to continue to monitor for lead data change. If there is data change (yes branch of block 314), then report generator component 252 is configured or programmed to automatically update the lead summary report using the changed lead data in block 316. Then flow 300 returns to block 312 to provide and save the updated lead summary report.

In this manner, lead summary reports are dynamic or live, and are not static reports, but may be continually updated under automatic computer-implemented program control. Consequently, the techniques herein provide ways to display, print or report about data in a continuous and updated manner as underlying data changes, which has not been practical or possible with past approaches.

Likewise, when the lead summary report is subsequently accessed (by the same or different user) and/or it is not currently being displayed, blocks 314 and/or 316 are performed as necessary.

Returning to block 304, if source(s) of the particular identified lead are known (yes branch of block 304), then report generator component 252 is configured or programmed to determine the relevant template and widgets corresponding to known source(s) by accessing the widget set definition 236 in block 320. The template and widget mappings for each of the sources (for example, fraud detection models) associated with the particular identified lead are obtained by the report generator component 252. In an embodiment, similar to the discussion above for block 306, the template for when sources are known is the same as the default template for when sources are unknown. Alternatively, the template for when sources are known may be different from the default template.

In an embodiment, when the particular identified lead is associated with a single particular source, then the widget set mapped to that particular source is used to generate the lead summary report. When the particular identified lead is associated with more than one source, then all the widgets specified in the widget set mapped to each of the respective sources are used to generate the lead summary report (without displaying the same widget more than once in the same report). For example, assume three different fraud detection models (model 1, model 2, and model 3) identified the particular identified lead as a potentially fraudulent lead. In the widget set definition 236, widgets A, B, C, and D are mapped to model 1, widgets A, B, C, E, and F are mapped to model 2, and widgets A, B, D, F, G, and H are mapped to model 3. Then the combined widget set that are displayed in the lead summary report comprises widgets A, B, C, D, E, F, G, and H. Widgets A and B may be common to most or all widget sets. For example, widget A may be the biographical information widget and widget B may be the notes and comments widget.

In some embodiments, even if a particular provider/member/pharmacist/claim is not considered to be sufficiently fraudulent by any single fraud detection model to be considered to be a potentially fraudulent lead, if the particular provider/member/pharmacist/claim is at or above a fraud threshold (which may be lower than for any given fraud detection model) for each of a certain number of or certain ones of the plurality of fraud detection models, then the particular provider/member/pharmacist/claim may be deemed to be a particular identified lead. This may be appropriate because fraud may not be clear cut and signs of fraud, while low individually, may signal fraud on a collective basis. All of the fraud detection models for which the threshold requirement is met are considered to be associated with the particular identified lead.

In another embodiment, where the particular identified lead is associated with more than one fraud detection model, report generator component 252 may is configured or programmed to apply weights to the plurality of fraud detection models associated with the particular identified leads. The applied weights may be different among these fraud detection models. The report generator component 252 is configured or programmed to determine whether each of the weighed fraud detection models is at or above a threshold. The weighed fraud detection models satisfying the threshold are reflected in the lead summary report, in that the widgets associated with those fraud detection models are included in the lead summary report. The widgets corresponding to the weighed fraud detection models below the threshold may not be included in the lead summary report. Weighting the fraud detection models may serve to limit the number of widgets included in the lead summary report to a manageable or reasonable number and/or display those widgets that may be the most relevant for accessing the particular identified lead.

In still another embodiment, where the particular identified lead is associated with more than one fraud detection model, report generator component 252 is configured or programmed to apply weights to the plurality of widgets corresponding to the fraud detection models associated with the particular identified leads. And then sorting the plurality of widgets to include or exclude in the lead summary report by similarly comparing against a threshold as discussed immediately above.

Once the relevant template and widgets are determined in block 320, the report generator component 252 obtains lead data specified by the (final) widget set from the data repositories 210 in block 322. Any data required by the template may also be obtained from the data repositories 210. In block 324, report generator component 252 dynamically generates a lead summary report for the particular identified lead using the relevant template, (final) widget set, lead data, and other relevant data. The lead summary report is dynamically generated similar to the discussion above for block 310.

Flow 300 proceeds to block 312 to provide and save the lead summary report generated in block 324.

In some embodiments, the lead summary report may include or may be associated with an overview page that may comprise, in one example, a table with one line per lead, with a hyperlink that identifies each specific lead summary report page. This table may also contain information about the model or source of each lead, and which analyst the lead was assigned to.

Figure 4:
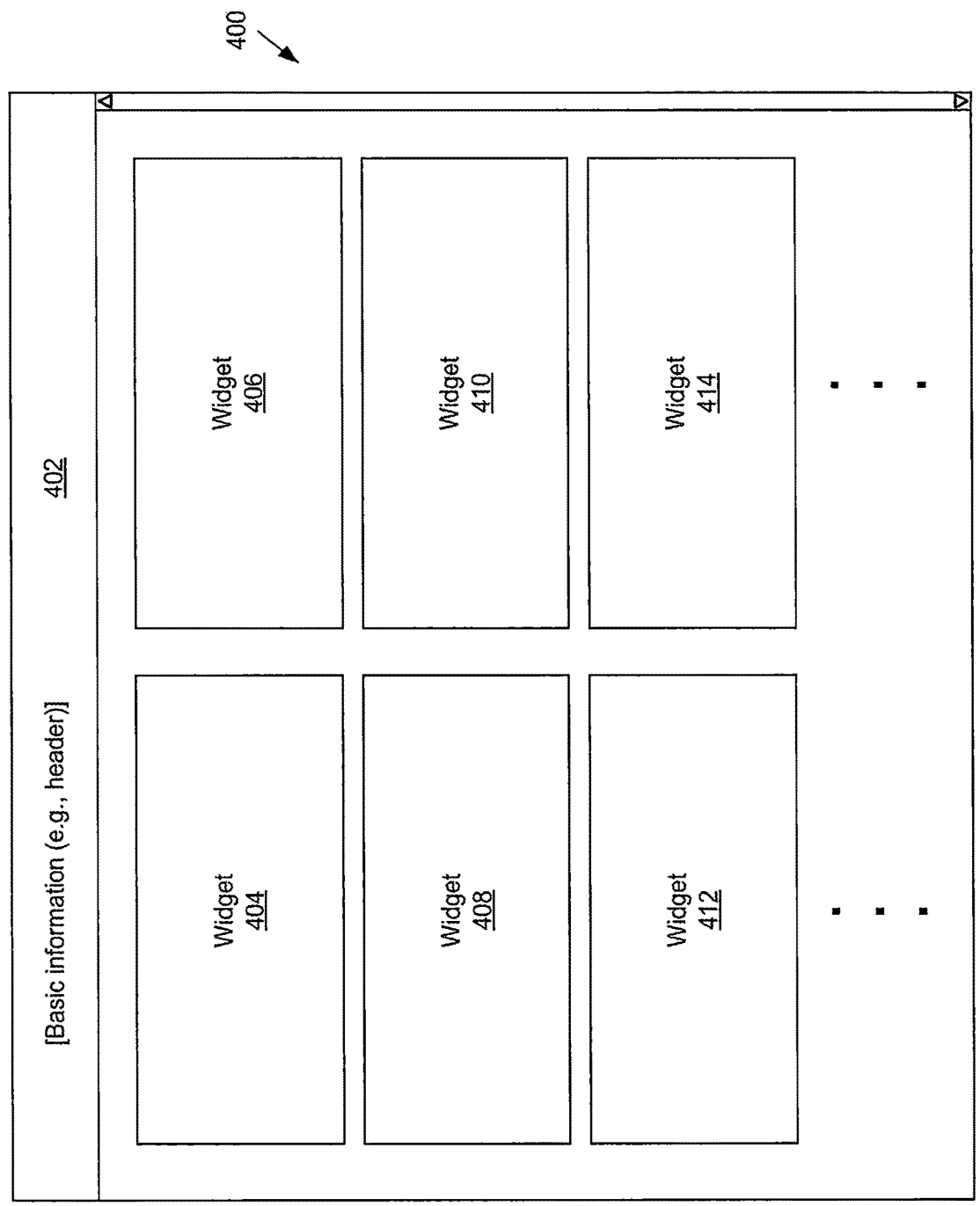
FIG. 4 illustrates an example lead summary report according to some embodiments.

FIG. 4 depicts an example lead summary report for the particular identified lead according to some embodiments.

As an example, lead summary report 400 includes a header section 402 and a plurality of widget panels or sections 404, 406, 408, 410, 412, 414. The report 400 also may be termed a lead report, lead summary, lead assessment document, lead assessment report.

The report 400 is configured in accordance with a report template that specifies the layout, format, content, content types, positions, sizes, embedded display elements, and other display elements. In an embodiment, report 400 may comprise a web page, portable document, word processing document, spreadsheet, other electronic document, JSON blob for rendering using an external system, or XML, dataset that may be interpreted or rendered using a browser of a client 106 or by an external system or program. Report 400 may also include UI elements such as tabs, menu options, pop up windows, scroll bar, more than one page, and/or the like. Although widget panels or sections 404-414 are depicted as being the same size and positioned relative to each other in accordance with a grid pattern, the lead data displayed in accordance with widgets 404-414 can be displayed in same or different sized panels relative to each other. The panels can also conform or not conform to a grid or other known pattern relative to each other.

Figure 5A:
Figure 5B:
Figure 5C:
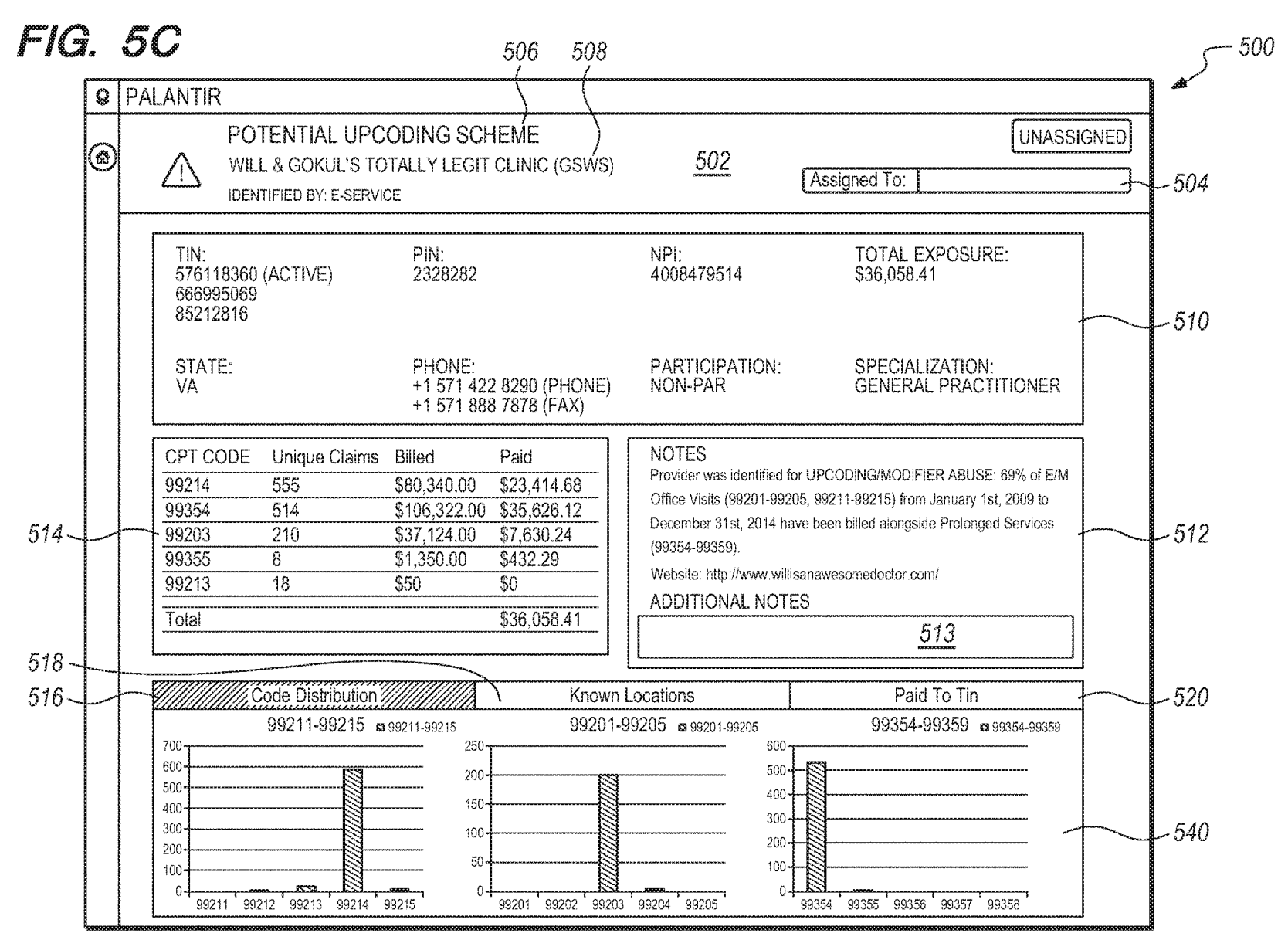

FIG. 5A, FIG. 5B, FIG. 5C illustrate an example lead summary report for the particular identified lead according to some embodiments.

In an embodiment, report 500 includes a header section 502, a plurality of widget panels or sections 510, 512, 514, 522, 530, 540, and a plurality of tabs 516, 518, 520. Header section 502 can include an analyst assignment element 504, a fraud detection model or scheme element 506, and/or a lead name element 508. Element 506 can identify the particular fraud detection model(s) or scheme(s) upon which the particular identified lead was deemed to be potentially fraudulent. As an example, element 506 may specify that the particular identified lead was found from the "upcoding" scheme. The analyst assignment element 504 can specify whether report 500 (and correspondingly the initial assessment of the particular identified lead) is assigned to a particular analyst or is unassigned. As depicted, report 500 is shown as unassigned. Alternatively, report 500 may be assigned to a particular analyst that has, for example, known expertise or is a specialist in assessing upcoding scheme frauds. Element 508 can include the name of the provider corresponding to the particular identified lead.

Widget panel 510 comprises an example of the biographical or basic provider information widget. In some embodiments, widget panel 510 may be included in most or all lead summary reports. Widget panel 512 comprises an example of the notes and comments widget. Widget panel 512 may include additional information about the associated fraud scheme(s) and/or free form information that the person or system that generated the particular identified lead deemed to be relevant. Widget panel 512 can include a notes/comments field 513 that the user can input with his/her notes, observations, recommendations, comments for the next person in the investigative chain, comments for the lead summary report design team, etc. about the report 500 and/or the particular identified lead. In some embodiments, widget panel 512 may be included in most or all lead summary reports. Widget panel 514 comprises an example of the top procedure (CPT) codes widget.

In some embodiments, report 500 may include a user feedback widget or the content of the user feedback widget may be included in widget panel 512. As an example, content of the user feedback widget may comprise, without limitation, a set of user feedback choices from which the user selects once review of the particular identified lead has been completed: "This lead is great, I recommend pursuing," "I had to do further digging but this lead is interesting enough to continue pursuing," "This lead is awful, don't provide more like these in the future," "I need more information to make a decision on this lead," or "Other." Providing a set number of textual feedback choices rather than a set of scores (for example, 1, 2, 3, 4, or 5 stars) or free form feedback options preemptively addresses potential scoring bias or manual review of user feedback for use in lead summary report design.

Widget panels 522, 530, 540 are displayed under tabs 518, 520, 516, respectively, according to an embodiment. Widget panel 522 comprises an example of the address view (map) widget. Widget panel 530 comprises an example of the paid to TIN widget. Widget panel 540 comprises an example of the procedure code breakdown or distribution widget. Alternatively, widget panels 522, 530, 540 may be displayed without tabs, may be displayed in additional page(s) of the report 500, and the like.

Although not shown, report 500 may include additional user interactive features. For example, report 500 may include a "freeze" button or other indicator for the user to create documentation based on the report 500.

Note that each widget is independent of the other widgets in the repot 500. Each of the widgets can display the same or different type of lead data or content from the other widgets, can display the lead data in the same or different format from the other widgets (tables, bar graph, line graph, text, map, input field, etc.), or otherwise be configured specific to the type of lead data that facilitates fraud or non-fraud determination or other assessment to be made by the user.

Figure 6:
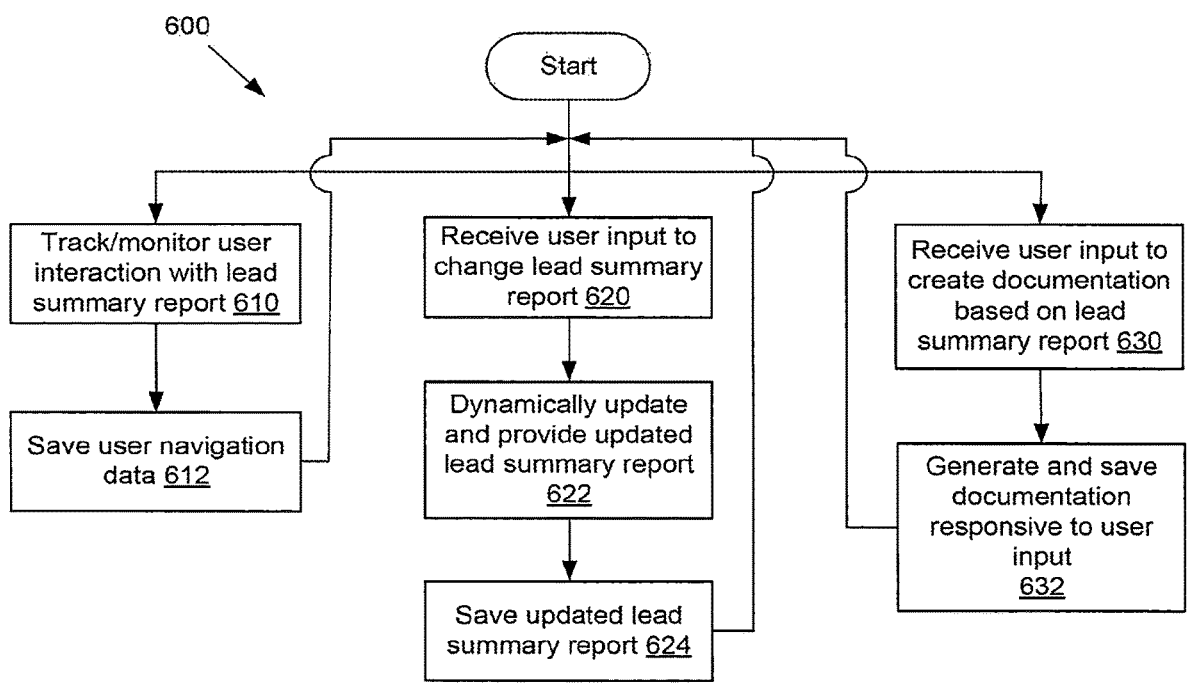
FIG. 6 illustrates an example flow or algorithm that may be programmed to capture data relating to user interaction taken on the dynamically generated lead summary reports, according to some embodiments.

FIG. 6 illustrates an example flow to capture data relating to user interaction taken on the dynamically generated lead summary reports, according to some embodiments. In an embodiment, each of the processes described in connection with the functional blocks of FIG. 6 may be implemented using one or more computer programs, other software elements, and/or digital logic in any of a general-purpose computer or a special-purpose computer, while performing data retrieval, transformation and storage operations that involve interacting with and transforming the physical state of memory of the computer. The flow 600 of FIG. 6 is described below in conjunction with the objects and components of FIG. 2, according to an embodiment. The process of flow 600 may be repeated for each of the respective lead summary reports.

During each session with the lead summary report (for example, as the report is displayed or accessed), monitor component 254 is configured or programmed to continually and in real-time monitors or tracks user's interaction, navigation, or actions taken on the lead summary report. Monitor component 254 is configured or programmed to track a plurality of factors relating to user interaction and records the tracked information in activity log 240, and in some instances, also in user defined data 242. In block 610, monitor component 254 is configured or programmed to track or monitor user interaction, navigation, and/or actions taken on the lead summary report such as, but not limited to: time spent viewing the lead summary report, start and end viewing times, how long the user spent on each given widget in the report, user inputs to the lead summary report, eye and/or mouse movement on the lead summary report, number of users that accessed the lead summary report, and a variety of other user interaction/navigation/actions taken on the lead summary report. The tracked information is saved in the activity log 240 at block 612.

The feedback and/or tracking information facilitates design of future lead summary reports. For example, if a particular widget is viewed longer or more frequent than other widgets, the particular widget may be included in more widget sets and/or the weight of that widget may be increased for a given model so that the widget is more likely to show up in other lead summary reports.

In addition to continually tracking user activity taken on the lead summary report, monitor component 254 is configured or programmed to respond to user inputs. In an embodiment, in block 620, monitor component 254, in conjunction with user interface component 250, is configured or programmed to receive user input to change the lead summary report. The user input can be entry of notes in the notes/comments section, selection of a feedback choice, assigning the report to a particular person, actuating a tab to view a particular widget, or otherwise affecting a change to the lead summary report and/or display of the lead summary report. In response, monitor component 254 in conjunction with the report generator component 252 is configured or programmed to dynamically update and provide the updated lead summary report accordingly at block 622. The change or updated information is saved in saved reports 238, activity log 240, and/or user defined data 242 as appropriate in block 624.

Moreover, in block 630, monitor component 254, in conjunction with user interface component 250, is configured or programmed to receive user input to create documentation based on the lead summary report (for example, "freeze" the report for evidentiary purposes). In response, monitor component 254 generates and saves the requested documentation in user defined data 242 in block 632.

In this manner, among other aspects, a computer-implemented process and computer system are provided that are configured or programmed for conveying lead data relating to suspected fraud, which have been identified using one or more fraud detection models or schemes in a meaningful context, to computers or users who may assess the identified leads. A lead summary report corresponding to a given identified lead is automatically and dynamically generated with information that specifically pertains to the given identified lead and optionally, to the particular fraud detection model(s) or scheme(s) from which the lead was identified. The lead-specific and model-specific data are configured in a plurality of widgets, each of the widgets designed to display a particular type of data in a format that is easy to understand. Thus, not only is medical claims data evidencing the fraudulency of the identified lead likely shown, the context in which the fraudulency was discovered is also provided to the extent possible. Lead summary report generation is possible for both same party- or third party-discovered leads. The automatically generated lead summary report also facilitates a variety of user input features to receive feedback information, create documentation based on the lead summary report, and to capture working notes and comments during assessment of the identified lead.

4.0 Implementation Example—Data Structures

The techniques described herein may be practiced with respect to medical claims data stored using a variety of different data structures and/or formats, depending on the embodiment. Example searchable data structures for storing medical claims data and other ancillary data records are described below. However, the examples given below are for illustrative purposes only, and the techniques described herein are not limited to any particular structures or formats.

In an embodiment, health care event objects are maintained in a health care event repository comprising one or more databases that store the health care event objects, provider objects are maintained in a provider repository comprising one or more databases that store the provider objects, patient objects are maintained in a patient repository comprising one or more databases that store the patient objects, and pharmacy objects are maintained a pharmacy repository comprising one or more databases that store the pharmacy objects. Other repositories may exist for other types of data objects. The one or more databases that constitute a repository may overlap between some or all of the repositories. Or, the repositories may be maintained separately.

In an embodiment, each of the objects described above, and other objects described herein, are generated from import operation(s) of data from various sources, such as an insurer's databases, a provider's health care records, pharmacy records, government records, and other public records. The import operation may be repeated periodically or on occasions to update the objects and/or add new objects. The import operation may involve various ETL operations that normalize the source data to fit data models such as described herein.

In an embodiment, some or all of the objects described herein are not necessarily stored in any permanent repository, but are rather generated from the source data "on demand" for the purpose of the various analyses described herein.

4.1 Logical Object Types

In an embodiment, a data object is a logical data structure that comprising values for various defined fields. A data object may be stored in a variety of underlying structure(s), such as a file, portions of one or more files, one or more XML elements, a database table row, a group of related database table row(s), and so forth. An application will read the underlying structure(s), and interpret the underlying structure(s) as the data object. The data object is then processed using various steps and algorithms such as described herein.

In one embodiment, the modeled object types conceptually include, without limitation: claim objects, such as medical physician claims, medical outpatient claims, medical inpatient claims, and pharmacy claims; patient objects; provider/prescriber objects; prescription objects; pharmacy objects; and fraud objects. Many variations on these combinations of objects are possible.

4.2 Sources

In an embodiment, some or all of the health care data objects are generated from source data hosted by a variety of sources. Example sources include provider or insurer sources such as: a claims processing database; a policy administration database, a provider network database, a membership/eligibility database, a claim account database, a pharmacy benefit database, a lab utilization gateway database, pharmacy claims database, an authentication call list, a tip-off hotline database, and a billing/accounts receivable database. Example sources further include government or public data repositories such as public health records, repositories of USPS zip codes, National Drug Codes, Logical Observation Identifiers Names and Codes, and/or National Provider Identifiers, an OIG exclusion list, and a List of Excluded Individuals/Entities. Of course, many other sources of data are also possible.

4.3 Databases

In an embodiment, data from the various data sources are passed through an ETL layer to form a set of databases. For example, the databases may include: Product, Organization, Geography, Customer, Member, Provider, Claim Statistics, Claim Aggregation, Claim Financial, Pharmacy Claims, Lab Results, and Revenue. The databases may store the various data objects described herein. The data objects may instead be arranged in a variety of other configurations.

4.4 Example Ontology

In an embodiment, an ontology for preventing health care fraud comprises the some or all of the following data object types: Claim objects, Drug objects, Member objects, Pharmacy objects, Plan Benefit objects, Prescriber objects, and Provider objects.

Each claim object represents a health care claim, which is a request for reimbursement from an insurer for health care expenses. There may be multiple types of claim objects, including claims objects for prescriptions, claim objects for laboratory tests, claim objects for medical procedures, and claim objects for other types of services. In an embodiment, a claim object comprises, among other elements, values for one or more the following types of attributes: unique system identifier(s), associated member identifier, allowed amount, claim status (paid, rejected, or reversed), date submitted, covered Medicare Plan D amount, date of service, estimated number of days prescription will last, paid dispensing fee, prescribed drug identifier, ingredient cost paid, mail order identifier, non covered plan paid amount, number of authorized refills, other payer amount, member plan type, amount paid by patient, deductible amount, pharmacy system identifier, prescriber system identifier, prescription written date, quantity dispensed, prescription claim number, service fee (the contractually agreed upon fee for services rendered), total amount billed by processor. Different fields may be specific to different types of providers or claims.

Each drug object represents a specific drug. In an embodiment, a drug object comprises, among other elements, values for one or more the following types of attributes: unique system identifier(s), American Hospital Formulary Service Therapeutic Class Code, generic status indicator (brand name or generic), drug name trademark status (trademarked, branded generic, or generic), dosage form, DEA class code, generic class name, over-the-counter indicator, drug strength, generic code number, generic code sequence, generic product index, maintenance drug code, product identifier qualifier, product service identifier, unit of measure, National Drug Code, and so forth.

Each member object represents a specific member of a health care plan. There may be multiple collections of members for different insurers and/or types of plans, and each collection may have a different structure. In an embodiment, a member object comprises, among other elements, values for one or more the following types of attributes: one or more unique system identifiers, maximum service month, the number of months enrolled in each particular year covered by the data (for example a different field for 2007, 2008, and so forth), first name, last name, gender, date of birth, address, city, state, zip code, county, telephone, social security number, additional address and other contact fields for different types of contact information (for example work, temporary, emergency, etc.), a plan benefit system identifier, an enrollment source system, and so forth.

In an embodiment, a member object may further include or be associated with tracking data that log changes to values for the above attributes over time. For example, a separate Member Detail object may exist, values for the above attributes for each month or year the member was covered by a plan. Each Member Detail object may include a month and/or year attribute and a member identifier to tie it back to its associated Member object.

Each pharmacy object represents a specific pharmacy. In an embodiment, a pharmacy object comprises, among other elements, values for one or more the following types of attributes: unique system identifier(s), pharmacy dispenser class (independent, chain, clinic, or franchise, government, alternate), pharmacy dispenser type (community/retail, long term, mail order, home infusion therapy, non-pharmacy, Indian health service, Department of Veterans Affairs, institutional, managed care, medical equipment supplier, clinic, specialty, nuclear, military/coast guard, compounding), affiliate code, service provider identifier, service provider identifier qualifier, and so forth.

Each plan benefit object represents a specific plan benefit. In an embodiment, a plan benefit object comprises, among other elements, values for one or more the following types of attributes: unique system identifier(s), contract number, provider identifier, start date, end date, package key, and so forth.

Each prescriber object represents a specific prescriber of drugs. In an embodiment, a plan benefit object comprises, among other elements, values for one or more the following types of attributes: unique system identifier(s), first name, last name, prescriber identifier(s), prescriber identifier qualifier(s) (for example not specified, NPI, Medicaid, UPIN, NCPDP ID, State License Number, Federal Tac ID, DEA, or State Issued), specialty code, and so forth. Prescriber objects and provider objects may in some cases represent or be associated with a same real world entity, but prescriber objects reflect data from a different source than provider objects. In some embodiments attributes from prescriber objects and provider objects may be combined into a single object. In other embodiments, the two objects are logically separate, but can be correlated together if they do in fact represent the same entity.

Each provider object represents a specific provider of health care services. In an embodiment, a provider object comprises, among other elements, values for one or more the following types of attributes: medical provider identification number (both text and numeric), provider type (medical professional, healthcare organization), provider status (active contract or no activate contract), various contract line indicators, one or more process exception hold effective dates, one or more process exception type codes, a date that the medical provider identification number was created, a date the provider record became inactive, an organization type code to indicate provided services or specialties, a Medicare identifier, provider medical degree, provider primary specialty, last name, first name, middle initial, name suffix, middle name, gender, social security number, federal tax identifier, date of birth, graduation date, medical school, credential status code, credential description, current credential cycle, current credential type (initial, re-credential, hospital-based, delegated, alliance, discontinued, empire initial, excluded from process, terminated), credential indicator, credential organization identifier, credential organization accreditation date, credential organization indicator, universal provider identifier, bill type (HCFA, UB92, UB04, composite), provider information source, provider claims classifier, email, last update type, address, and so forth.

Additional data objects that may be in a health care ontology are set forth in the attached appendix.

4.5 Metrics

Various example metrics for automatically identifying, prioritizing, and/or investigating leads are described below. In an embodiment, metrics may be utilized in formulating certain searches, such that claim records may be located based on how various claim attributes compare to various metrics. In an embodiment, metrics may be directly searchable. In an embodiment, metrics may be calculated and displayed in various visualization interfaces associated with search results. For instance, metrics may be calculated for a set of search results, and/or data from a search result may be compared to metrics for a group of records at large. Metrics may be calculated and stored periodically, or calculated on demand.

Metrics related to member objects may include, without limitation, one or more of: an average and/or standard deviation of Schedule 2 prescriptions per month; a count of drug abuse diagnoses; a count, average, and/or standard deviation of ER visits per year; a count of distinct providers that have written prescriptions for the member; a count of distinct pharmacies that have filled prescriptions for the member; a sum amount paid by an insurer on behalf of the member; an average and/or standard deviation amount paid per month; a sum number of pills dispensed per month; an average days between prescriptions; an average and/or standard deviation prescriptions per month for the member; an average and/or standard deviation for member medical claims per month; a count of total Schedule 2 prescriptions; a count of total Schedule 3 prescriptions; a count of total prescriptions; an average and/or standard deviation for net amount paid per diagnosis category; a count of durable medical equipment claims; a count of methadone overdoses; a count of opiate poisoning; a methadone dependence indicator; and/or a sum DME Net Amount paid.

Metrics related to provider objects may include, without limitation, one or more of: an average and/or sum total billed by provider; a sum net amount paid to the provider; an average and/or standard deviation net amount paid per month; a standard deviation for net amount paid per month by specialty; a standard deviation for net amount paid per month by specialty by geography, an average prescription pill quantity; an average prescription number of refills; a count of prescription claims not paid; a count of prescription claims; a count of medical claims; an average and/or standard deviation for prescription claims per patient; an average and/or standard deviation for medical claims per patient; a percentage of Schedule 2 drugs; a percentage of Schedule 3 drugs; a percentage of Schedule 2 drugs by specialty; a percentage of Schedule 3 drugs by specialty; a count of distinct patients of the provider; a count of distinct pharmacies to which patients of the provider are sent; a standard deviation of distinct diagnoses made by the provider by specialty; a count of distinct procedures performed by the provider; a count of clinic ownerships; a standard deviation for net amount paid to the provider by diagnosis; a count of durable medical equipment prescriptions made; a percentage of in-network claims attributed to the provider; and/or an estimated total days in business.

Metrics related to provider objects may further include, without limitation, one or more of: average claims per day; average net amount paid per claim; average net amount paid per month; average patient count; average pharmacy count; distinct count of diagnoses; a histogram of diagnoses; distinct count of procedures; and/or a histogram of procedures.

Metrics related to pharmacy objects may include, without limitation, one or more of: average net amount paid by the insurer; maximum and/or average net amount paid per prescriber; count of claims; percentage of filled prescriptions that involved a Schedule 2 category of drugs; percentage of filled prescriptions that involved a Schedule 3 category of drugs; average and/or sum dispensing fee; days in business, percentage of filled prescriptions that involved a brand name drug; a count of distinct drug names in the prescriptions; percentage of filled prescriptions that involved a high reimbursement drug; percentage of filled prescriptions that involved a drug of potential abuse; a percentage of claims for refills; average and/or standard deviation distance traveled by customers to the pharmacy; a count of co-located pharmacies; percentage of filled prescriptions that involved small refills; percentage of claims that were reversed; a count of claims not paid; average billed per patient; average billed per prescriber; average claims per patient; average claims per prescriber.

Metrics related to diagnosis objects may include, without limitation, one or more of: a histogram of CPT-4, ICD-9, ICD-10 or HCPCS procedures; a histogram of co-occurring diagnoses; average net amount paid per year per patient; average total net amount paid per patient; a histogram of drug names prescribed; an indicator of drug abuse; and/or an indicator of drug-seeking behavior.

Metrics related to procedure objects may include, without limitation, one or more of: a histogram of diagnoses; a histogram of co-occurring procedures on the same date per patient; and a total, average, minimum, and/or maximum procedure count per patient per diagnosis.

Metrics related to drug objects may include, without limitation, one or more of: maximum drug quantity per patient per year; and/or minimum, maximum, and/or average net amount paid.

Metrics related to prescription claim objects may include, without limitation, one or more of: distance traveled to pharmacy; distance traveled to prescriber; an indicator of whether the prescription is for a drug of abuse; a standard deviation of net amount paid; an indicator of whether the prescribed patient's gender is appropriate to the prescription; an indicator of whether the prescription claim is for an expensive branded drug; and/or an indicator of whether the prescription claim is for a Schedule 2 commonly abused drug.

Metrics related to medical claim objects may include, without limitation, one or more of: distance traveled to physician; an indicator of whether the claim is indicative of drug abuse; and/or a standard deviation of net amount paid per procedure.

In an embodiment, various triggers may be generated based on the above metrics. The triggers are monitored functions of one or more of the metrics. When a monitored function has a value that is within a particular range, the trigger identifies one or more lead objects that are associated with the one or more metrics.

For example, in an embodiment, triggers may include members visiting three of more independent pharmacies in a day, members obtaining prescriptions in three of more states within a month, or members receiving multiple and subsequent home rental medical equipment. Each of these triggers would produce a member lead object. Another example trigger is multiple new patient office visits for the same patient in a three year period. This trigger would produce a member lead object.

An additional example of a trigger is a Top Pharmacies by Drugs Commonly Abused trigger. For each month, this trigger lists the pharmacy that has dispensed the most amount of one of the commonly abused drugs. An additional example of a trigger is a Top Patients Receiving Drugs Commonly Abused trigger. For each month, this trigger lists the patient receiving the most amount of one of the commonly abused drugs. An additional example of a trigger is a Top Prescribers of Drugs Commonly Abused trigger. This trigger lists the providers who have prescribed the most amount of one of the most commonly abused drugs. An additional example of a trigger is a Mailbox Matching trigger. For each region of interest (as denoted by a City and State), this trigger lists providers who have a practice address that matches the location of a UPS drop box. An additional example of a trigger is a Frequent NPIs trigger. For each region of interest (as denoted by a City and State), this trigger lists provider locations receiving multiple NPIs in a short time frame.

5.0 Hardware Overview

According to one embodiment, the techniques described herein are implemented by one or more special-purpose computing devices. The special-purpose computing devices may be hard-wired to perform the techniques, or may include digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, portable computer systems, handheld devices, networking devices or any other device that incorporates hard-wired and/or program logic to implement the techniques.

Figure 7:
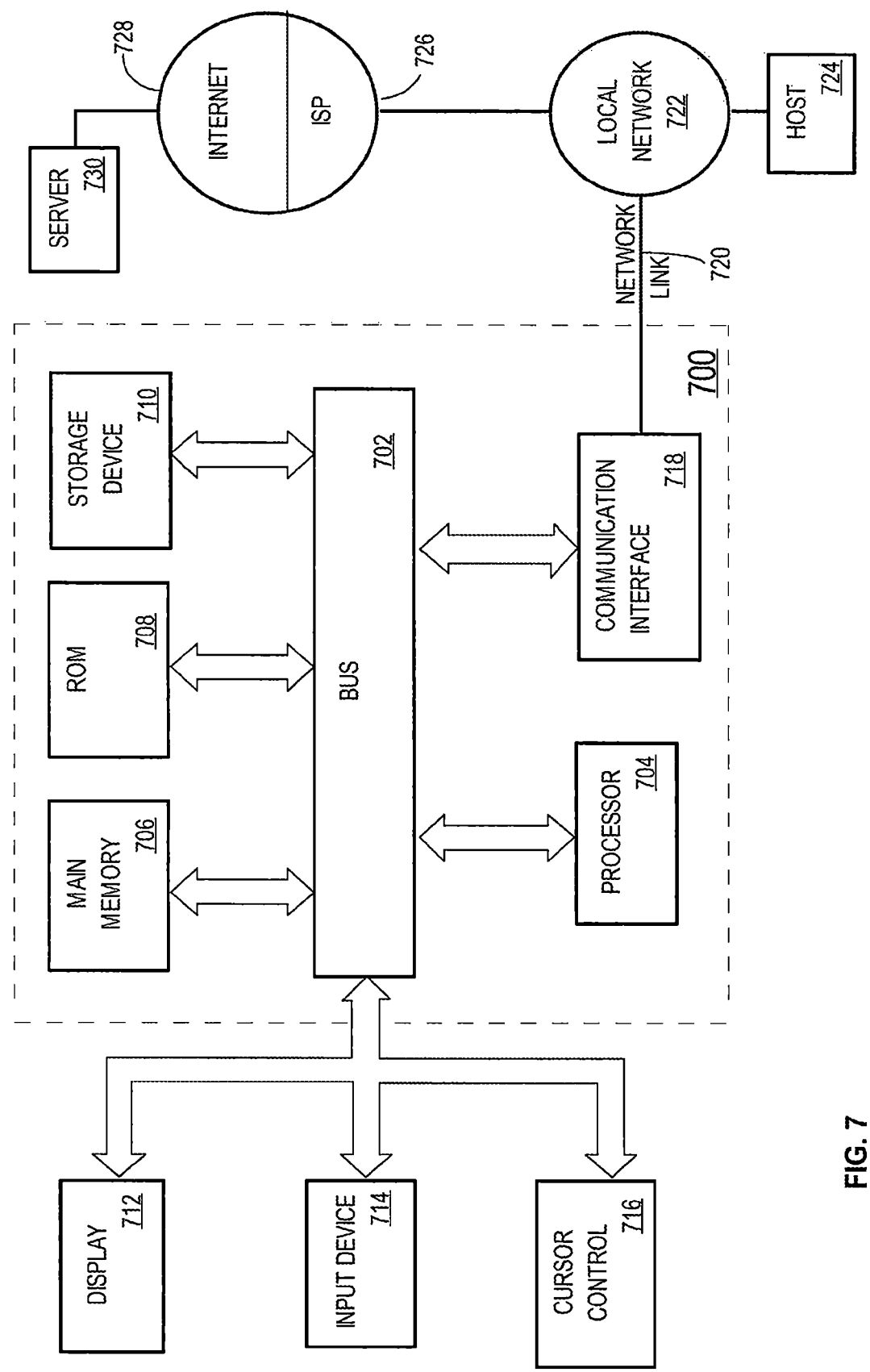
FIG. 7 illustrates a block diagram of an example computer system upon which embodiments of the present disclosure may be implemented.

For example, FIG. 7 is a block diagram that illustrates a computer system 700 upon which embodiments of the present disclosure may be implemented. System 100, server 102, database 104, clients 106, or system 200 are examples of computer system 700. Computer system 700 includes a bus 702 or other communication mechanism for communicating information, and a hardware processor 704 coupled with bus 702 for processing information. Hardware processor 704 may be, for example, a general purpose microprocessor.

Computer system 700 also includes a main memory 706, such as a random access memory (RAM) or other dynamic storage device, coupled to bus 702 for storing information and instructions to be executed by processor 704. Main memory 706 also may be used for storing temporary variables or other intermediate information during execution of instructions to be executed by processor 704. Such instructions, when stored in non-transitory storage media accessible to processor 704, render computer system 700 into a special-purpose machine that is customized to perform the operations specified in the instructions.

Computer system 700 further includes a read only memory (ROM) 708 or other static storage device coupled to bus 702 for storing static information and instructions for processor 704. A storage device 710, such as a magnetic disk or optical disk, is provided and coupled to bus 702 for storing information and instructions.

Computer system 700 may be coupled via bus 702 to a display 712, such as a cathode ray tube (CRT) or liquid crystal display (LCD), for displaying information to a computer user. An input device 714, including alphanumeric and other keys, is coupled to bus 702 for communicating information and command selections to processor 704. Another type of user input device is cursor control 716, such as a mouse, a trackball, or cursor direction keys for communicating direction information and command selections to processor 704 and for controlling cursor movement on display 712. This input device typically has two degrees of freedom in two axes, a first axis (for example, x) and a second axis (for example, y), that allows the device to specify positions in a plane.

Computer system 700 may implement the techniques described herein using customized hard-wired logic, one or more ASICs or FPGAs, firmware and/or program logic which in combination with the computer system causes or programs computer system 700 to be a special-purpose machine. According to one embodiment, the techniques herein are performed by computer system 700 in response to processor 704 executing one or more sequences of one or more instructions contained in main memory 706. Such instructions may be read into main memory 706 from another storage medium, such as storage device 710. Execution of the sequences of instructions contained in main memory 706 causes processor 704 to perform the process steps described herein. In alternative embodiments, hard-wired circuitry may be used in place of or in combination with software instructions.

The term "storage media" as used herein refers to any non-transitory media that store data and/or instructions that cause a machine to operation in a specific fashion. Such storage media may comprise non-volatile media and/or volatile media. Non-volatile media includes, for example, optical or magnetic disks, such as storage device 710. Volatile media includes dynamic memory, such as main memory 706. Common forms of storage media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge.

Storage media is distinct from but may be used in conjunction with transmission media. Transmission media participates in transferring information between storage media. For example, transmission media includes coaxial cables, copper wire and fiber optics, including the wires that comprise bus 702. Transmission media can also take the form of acoustic or light waves, such as those generated during radio-wave and infra-red data communications.

Various forms of media may be involved in carrying one or more sequences of one or more instructions to processor 704 for execution. For example, the instructions may initially be carried on a magnetic disk or solid state drive of a remote computer. The remote computer can load the instructions into its dynamic memory and send the instructions over a telephone line using a modem. A modem local to computer system 700 can receive the data on the telephone line and use an infra-red transmitter to convert the data to an infra-red signal. An infra-red detector can receive the data carried in the infra-red signal and appropriate circuitry can place the data on bus 702. Bus 702 carries the data to main memory 706, from which processor 704 retrieves and executes the instructions. The instructions received by main memory 706 may optionally be stored on storage device 710 either before or after execution by processor 704.

Computer system 700 also includes a communication interface 718 coupled to bus 702. Communication interface 718 provides a two-way data communication coupling to a network link 720 that is connected to a local network 722. For example, communication interface 718 may be an integrated services digital network (ISDN) card, cable modem, satellite modem, or a modem to provide a data communication connection to a corresponding type of telephone line. As another example, communication interface 718 may be a local area network (LAN) card to provide a data communication connection to a compatible LAN. Wireless links may also be implemented. In any such implementation, communication interface 718 sends and receives electrical, electromagnetic or optical signals that carry digital data streams representing various types of information.

Network link 720 typically provides data communication through one or more networks to other data devices. For example, network link 720 may provide a connection through local network 722 to a host computer 724 or to data equipment operated by an Internet Service Provider (ISP) 726. ISP 726 in turn provides data communication services through the world wide packet data communication network now commonly referred to as the "Internet" 728. Local network 722 and Internet 728 both use electrical, electromagnetic or optical signals that carry digital data streams. The signals through the various networks and the signals on network link 720 and through communication interface 718, which carry the digital data to and from computer system 700, are example forms of transmission media.

Computer system 700 can send messages and receive data, including program code, through the network(s), network link 720 and communication interface 718. In the Internet example, a server 730 might transmit a requested code for an application program through Internet 728, ISP 726, local network 722 and communication interface 718.

The received code may be executed by processor 704 as it is received, and/or stored in storage device 710, or other non-volatile storage for later execution.

In the foregoing specification, embodiments of the invention have been described with reference to numerous specific details that may vary from implementation to implementation. The specification and drawings are, accordingly, to be regarded in an illustrative rather than a restrictive sense. The sole and exclusive indicator of the scope of the invention, and what is intended by the applicants to be the scope of the invention, is the literal and equivalent scope of the set of claims that issue from this application, in the specific form in which such claims issue, including any subsequent correction.

What is claimed is:

1. A computer-implemented method comprising:
 in response to receiving lead data identifying an entity associated with a health care claim relating to suspected fraud, determining one or more sources that were used to identify the entity or the suspected fraud;

determining a plurality of data display elements based on the one or more sources, wherein each of the plurality of data display elements is configured to cause displaying health care claims data associated with the entity in a designated format;

applying a weight to each of the plurality of data display elements based upon historical levels of user interaction with each of the plurality of data display elements displayed within historical lead summary reports;

determining a subset of the plurality of data display elements based on whether weights of each of the plurality of data display elements is at or above at least one threshold, wherein each data display element in the subset satisfies the at least one threshold;

automatically obtaining, from a data repository, specific health care claims data associated with the entity for each of the plurality of data display elements in the subset;

generating a lead summary report associated with the entity using a report template, the subset, and the specific health care claims data;

wherein the method is performed using one or more computing devices.

2. The method of claim 1, further comprising automatically updating the lead summary report in response to detecting a change in the specific health care claims data.

3. The method of claim 1, further comprising:
receiving input from a client computing device specifying a change to the lead summary report;
responsive to the input, updating the lead summary report with the change.

4. The method of claim 3, wherein the input comprises adding notes or comments to the lead summary report, assigning the lead summary report to a particular user for assessment, or selection of a feedback option.

5. The method of claim 1, further comprising creating and digitally storing one or more evidentiary documents based on the lead summary report, in response to an input from a client computing device specifying to preserve the lead summary report at a certain point in time.

6. The method of claim 1, wherein each of the one or more sources comprises a fraud detection model or scheme.

7. The method of claim 1, wherein the determining which one or more sources comprises determining that a source is unknown and that the suspected fraud was identified by a third party computer system, and wherein the subset comprises a particular subset that is pre-defined for use when the source is unknown.

8. The method of claim 1, wherein the determining which one or more sources comprises determining a particular source from among a plurality of sources.

9. The method of claim 1 wherein the applying the weight to the each of the plurality of data display elements is in response to determining that a total number of the plurality of data display elements exceeds a limit to a number of data display elements to be included on the lead summary report, and wherein the determining the subset of the plurality of data display elements based on whether the weights of each of the plurality of data display elements is at or above the at least one threshold comprises determining whether each of the plurality of data display elements is most relevant for accessing the entity.

10. The method of claim 1, wherein the lead summary report comprising an overview page containing hyperlinks to specific display elements of the subset and information about sources of the one or more sources.

11. A system comprising:
one or more databases including a plurality of health care claims data and a plurality of data display elements;

a report generator component, at least partially implemented by computing hardware, coupled to the one or more databases and comprising one or more sequences of instructions which when executed by one or more processors are programmed to perform:

in response to receiving lead data identifying an entity associated with a health care claim relating to suspected fraud, determining one or more sources that were used to identify the entity or the suspected fraud;

determining a plurality of data display elements based on the one or more sources, wherein each of the plurality of data display elements is configured to cause displaying health care claims data associated with the entity in a designated format;

applying a weight to each of the plurality of data display elements based upon historical levels of user interaction with each of the plurality of data display elements displayed within historical lead summary reports;

determining a subset of the plurality of data display elements based on whether weights of each of the plurality of data display elements is at or above at least one threshold, wherein each data display element in the subset satisfies the at least one threshold;

automatically obtaining, from a data repository, specific health care claims data associated with the entity for each of the plurality of data display elements in the subset;

generating a lead summary report associated with the entity using a report template, the subset, and the specific health care claims data.

12. The system of claim 11, wherein the report generator component is programmed to automatically update the lead summary report in response to detecting a change in the specific health care claims data.

13. The system of claim 11, further comprising sequences of instructions which are programmed, when executed by the one or more processors, to cause:
receiving input from a client computing device specifying a change to the lead summary report;
responsive to the input, updating the lead summary report with the change.

14. The system of claim 13, wherein the input comprises adding notes or comments to the lead summary report, assigning the lead summary report to a particular user for assessment, or selection of a feedback option.

15. The system of claim 11, further comprising sequences of instructions which are programmed, when executed by the one or more processors, to cause creating and digitally storing one or more evidentiary documents based on the lead summary report, in response to an input from a client computing device specifying to preserve the lead summary report at a certain point in time.

16. The system of claim 11, wherein each of the one or more sources comprises a fraud detection model or scheme.

17. The system of claim 11, wherein the determining which one or more sources comprises determining that a source is unknown and that the suspected fraud was identified by a third party computer system, and wherein the subset comprises a particular subset that is pre-defined for use when the source is unknown.

18. The system of claim 11, wherein the determining which one or more sources comprises determining a particular source from among a plurality of sources.

19. The system of claim 11 wherein the applying the weight to the each of the plurality of data display elements is in response to determining that a total number of the plurality of data display elements exceeds a limit to a number of data display elements to be included on the lead summary report, and wherein the determining the subset of the plurality of data display elements based on whether the weights of each of the plurality of data display elements is at or above the at least one threshold comprises determining whether each of the plurality of data display elements is most relevant for accessing the entity.

20. The system of claim 11, wherein the lead summary report comprising an overview page containing hyperlinks to specific display elements of the subset and information about sources of the one or more sources.

\* \* \* \* \*